United States Patent
Lee

(10) Patent No.: US 10,127,691 B2
(45) Date of Patent: Nov. 13, 2018

(54) GEOMETRY CORRECTION FOR COMPUTED TOMOGRAPHY

(71) Applicant: The Boeing Company, Chicago, IL (US)

(72) Inventor: James H. Lee, Ravensdale, CA (US)

(73) Assignee: The Boeing Company, Chicago, IL (US)

( * ) Notice: Subject to any disclaimer, the term of this patent is extended or adjusted under 35 U.S.C. 154(b) by 86 days.

(21) Appl. No.: 15/357,028

(22) Filed: Nov. 21, 2016

(65) Prior Publication Data

US 2018/0144511 A1 May 24, 2018

(51) Int. Cl.
*G06T 11/00* (2006.01)
*G01N 23/046* (2018.01)
*G06T 7/00* (2017.01)

(52) U.S. Cl.
CPC .......... *G06T 11/005* (2013.01); *G01N 23/046* (2013.01); *G06T 7/003* (2013.01)

(58) Field of Classification Search
CPC .. G06T 7/30; G06T 7/33; G06T 7/337; G06T 7/70; G06T 7/73; G06T 7/74; G06T 11/005; G01N 23/0461; A61B 6/03; A61B 6/032; A61B 6/5205; A61B 6/5258
See application file for complete search history.

(56) References Cited

U.S. PATENT DOCUMENTS

| 4,703,424 A | 10/1987 | Gullberg et al. ............. 364/414 |
| 2004/0167387 A1 | 8/2004 | Wollenweber et al. ...... 600/407 |
| 2016/0239971 A1 | 8/2016 | Yu et al. ............... G06T 7/0024 |
| 2018/0068467 A1* | 3/2018 | Wang et al. .......... G06T 11/005 |

OTHER PUBLICATIONS

Peters, Terry, "CT Image Reconstruction", Robarts Research Institute, Retrieved from the Internet: https://www.aapm.org/meetings/02AM/pdf/8372-23331.pdf, Accessed on Sep. 12, 2016, 2011, 49 pgs.
"U.S. Appl. No. 15/357,109, Ex Parte Quayle Action mailed Apr. 18, 2018", 7 pages.

* cited by examiner

*Primary Examiner* — Andrew W Johns
(74) *Attorney, Agent, or Firm* — Kwan & Olynick LLP

(57) ABSTRACT

Disclosed are apparatus and methods determining a center offset distance for computed tomography (CT) imaging. A specimen is positioned between an emission source for outputting radiation towards the specimen while the specimen rotates with respect to a detector for receiving radiation that has passed through the specimen. A center calibration indicator (CCI) is also positioned near the specimen so that at least a portion of the radiation passes through the CCI onto the detector. Projection data is collected from emissions received at the detector for multiple rotational positions of the specimen relative to the detector. A sinogram image is generated based on the projection data. Two alignment points corresponding to the CCI are located in the sinogram and used to determine the center offset distance for the sinogram. A specimen image is reconstructed by back projecting the sinogram using the determined center offset distance.

20 Claims, 20 Drawing Sheets

GEOMETRY CORRECTION FOR COMPUTED TOMOGRAPHY

TECHNICAL FIELD

The present invention relates generally to methods and systems for computed tomography (CT) and, more specifically, to center offset calibration for image reconstruction in such CT systems.

BACKGROUND

A CT system is one that takes a series of 2D radiographs of an object or person as the part or person rotates relative to the radiography system (e.g. an X-ray source and imaging system). These images are known as a "set of projections". The CT system then uses the projections and creates a 3D data set known as a "volume data set". The creation of the 3D data set is known as "reconstruction". This data set can be viewed in many ways, but primarily thin sections of the data set are used to create images known as "slices".

One purpose of a CT system is to provide slices of an object or specimen, such as providing slices of a patient's brain as part of a medical diagnostic procedure. Another use of a CT system is to provide slices of a manufactured component or system for quality control purposes.

The object can be rotated using a rotatable platform while such object is being imaged. One part of a typical image reconstruction process depends on the center of rotation being aligned with respect to the center of the source of radiation (known as the "spot") and the center of the detector. Portions of the resulting reconstructed image may be difficult to reconstruct properly due to various reasons, including an undesirable offset in the center of rotation. Blurring of features of the object will then occur during reconstruction.

In view of the foregoing, improved center offset calibration techniques for image analysis for CT systems would be beneficial.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of determining a center offset distance for computed tomography (CT) imaging is disclosed. A specimen is provided on a support that is positioned between an emission source for outputting radiation towards the specimen while the specimen rotates with respect to a detector for receiving radiation that has passed through the specimen. A center calibration indicator (CCI) is also positioned near the specimen so that at least a portion of the radiation passes through the CCI and impinges on the detector. Projections are collected from emissions received at the detector for a plurality of rotational positions of the specimen relative to the detector. A sinogram image is generated based on the projections. Two alignment points corresponding to the CCI are located in the sinogram, and the center offset distance for the sinogram image is determined based on their positions. An image of the specimen may then be reconstructed from the sinogram image using the determined center offset distance. In one example, the CCI is attached to the specimen, and is sized so that radiation passes through an entire length of the CCI at two rotational positions corresponding to the two alignment points being attenuated more than other points in the sinogram image.

In one implementation, the center offset distance is determined by comparing a center of the sinogram image to a midway position between the two located alignment points. In another example, the CCI is sized and shaped to result in two opposing points of contrast in the sinogram image that together accurately depict the center offset distance. In another embodiment, the CCI has a different density than the specimen. In another aspect, the CCI is a thin rectangular object having a significantly longer length than thickness.

In another implementation, the center offset distance is determined by (i) counting a first number of pixels from a first one of the two located alignment points to a closest edge of the sinogram image, (ii) converting the first pixel number into a first distance based on a size of the detector and a magnification of the projection data, (iii) counting a second number of pixels from a second one of the two located alignment points to a closest edge of the sinogram image, (iv) converting the second pixel number into a second distance based on a size of the detector and a magnification of the projection data, and (v) comparing the first distance to the second distance to obtain the center offset distance, including polarity.

In yet another embodiment, the center offset distance is determined to correspond to a fraction of a detector element of the detector. In another aspect reconstructing the image of the specimen includes entering the offset distance, including its polarity, into geometry data for the sinogram image. In another embodiment, reconstructing the image of the specimen includes (i) determining whether the determined offset distance differs by a predefined limit from an offset calculated by a CT technique that is not based on the CCI, (ii) reconstructing the image using the CT technique's calculated offset if the predefined limit is not exceeded, and (iii) reconstructing the image using the determined center offset distance if the predefined limit is exceeded.

In an alternative embodiment, the invention pertains to a computed tomography (CT) system. The system includes an emission source for outputting radiation towards a specimen and a support for placement of the specimen and that is rotatable. A center calibration indicator (CCI) is positioned near the specimen so that at least a portion of the radiation passes through the CCI and impinges on a detector, which is configured for receiving radiation that has passed through the specimen and CCI, and a processor and memory configured for performing one or more of the above-described method operations.

These and other aspects of the invention are described further below with reference to the Figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction

Figure 1:
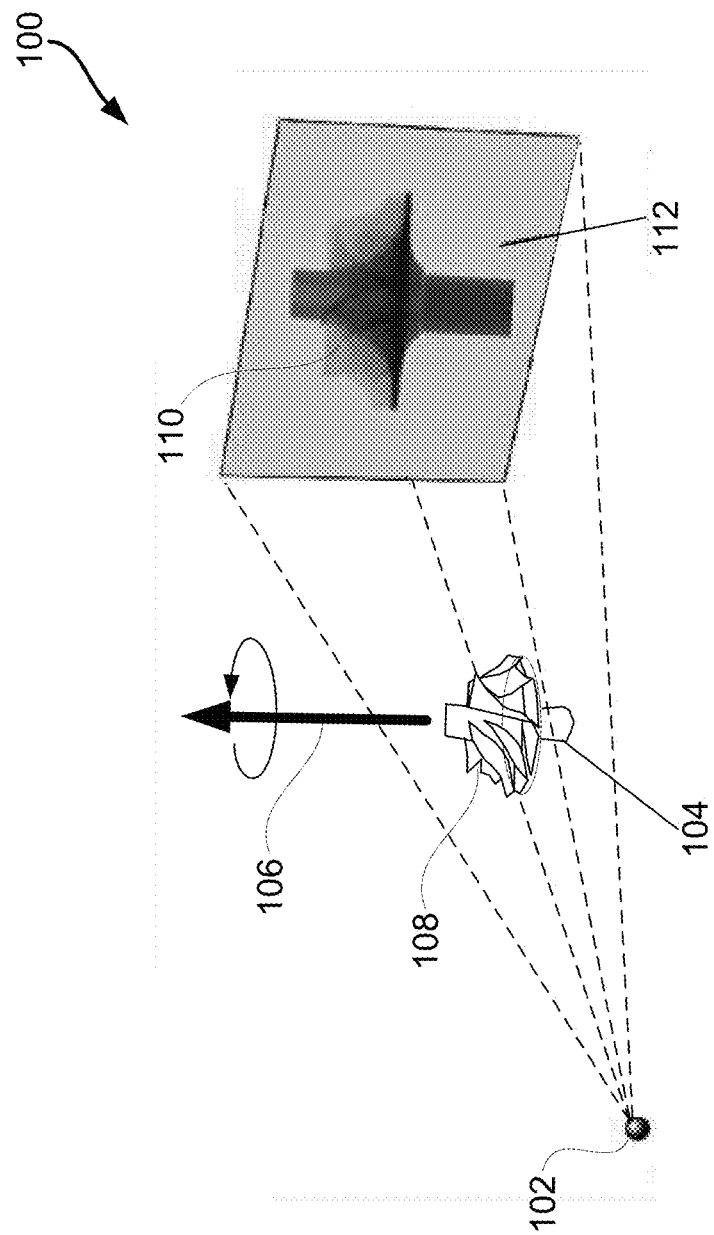
FIG. 1 is a diagrammatic representation of a CT imaging system.

FIG. 1 is a diagrammatic representation of a CT imaging system 100. As shown, the CT system 100 may include a radiation source 102 for directing penetrating radiation towards a specimen 108. For instance, the radiation source 102 may take the form of an X-ray tube. The radiation emitted by the radiation source may also be shaped so as to be collimated into a fan or rays. The system 100 also includes a support 104 upon which the specimen is placed. The support 104 also may take the form of movement mechanism (e.g., turn table) for rotating the specimen 108, for example, around rotational axis 106. The rays pass through different portions of the specimen 108 as it rotates. The radiation becomes attenuated due to different densities of the material of the specimen through which the radiation passes.

The radiation passes through the rotating specimen; is attenuated in various amounts by the object; and then impinges on a radiation detector 112. The radiation detector 112 may take any suitable form that receives radiation, such as X-rays, passing through an object and generates signals or images corresponding to emission attenuation for particular positions in the specimen. For instance, a gamma camera having a crystal face may be positioned to receive the X-rays that pass through the specimen and impinge on such camera.

The images created by the attenuated radiation at different angles (one projection per angular position) are pixelated 2D images 110 representing the linear attenuation coefficients of the sample through which the radiation has passed. In one technique, a sinogram image is formed based on the attenuated data that is collected at the different angles of rotation. The sinogram image is then used during reconstruction.

FIGS. 2A through 2D are diagrammatic illustrations of a general process for reconstructing an image based on the projections obtained at different angles of a sample with respect to a detector. Although a heavy industrial component would typically be rotated with respect to the detector, this example shows the detector rotating around the sample, which is equivalent to rotating the object, so as to simplify the drawings.

Figure 2A:
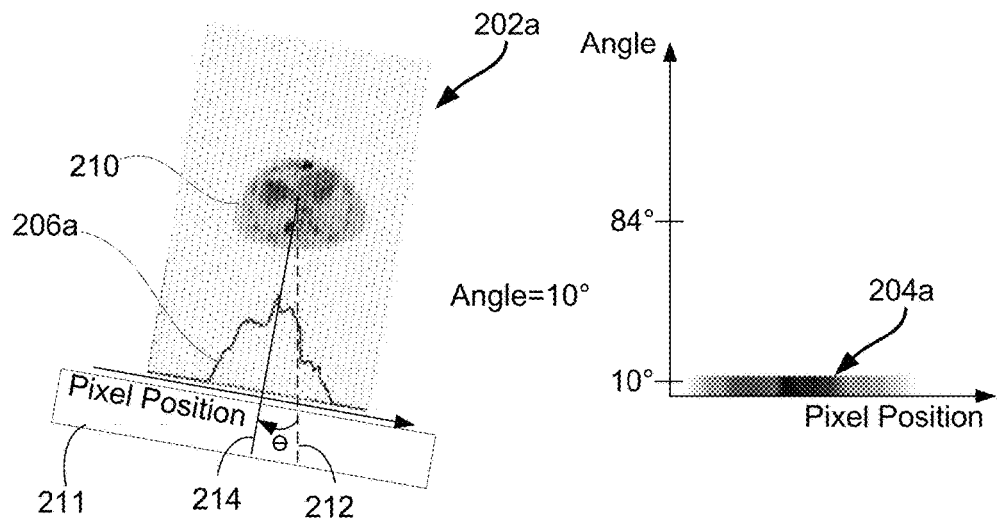
FIG. 2A through 2D are diagrammatic illustrations of a process for reconstructing an image based on the projections obtained at different angles of a sample with respect to a detector.
Figure 2B:
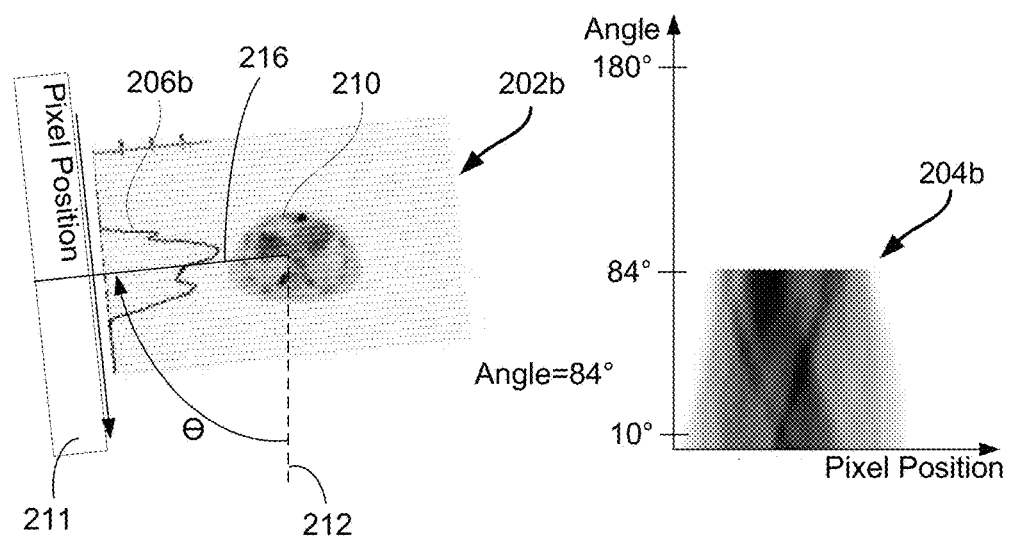
Figure 2C:
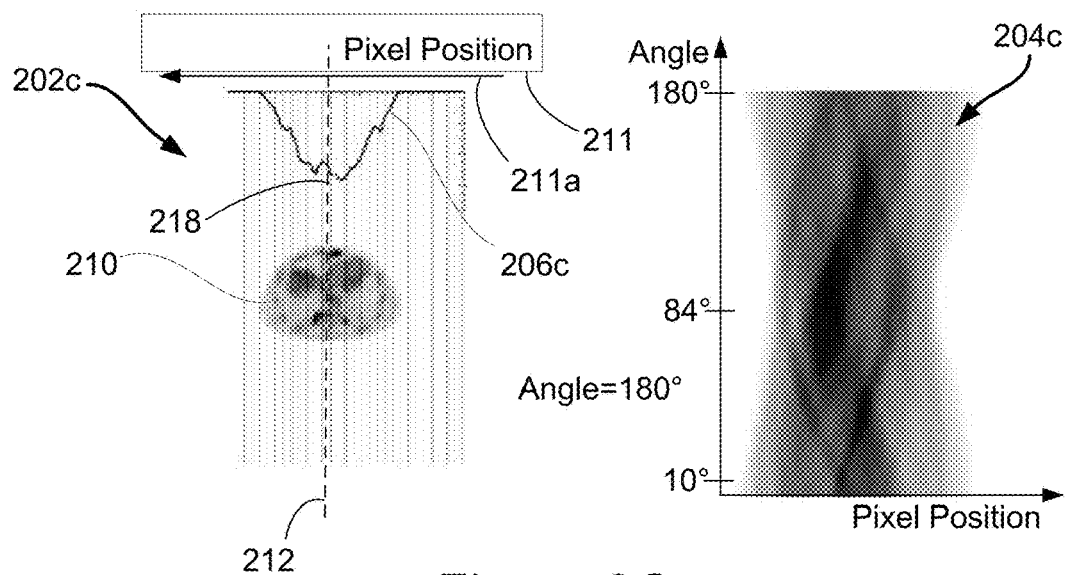

In general, emission data is collected at the detector 211 as it rotates with respect to sample 210. The emission data is used to construct a 2D sinogram (e.g., 204a-204c), which represents the emission data as a function of rotation angle $\Theta$. As shown in FIG. 2A, the detector 211 and sample 210 have a first orientation 202a with respect to each other. More specifically, the rotation angle $\Theta$ is measured with respect to a first reference axis 212. In FIG. 2A, the detector 211 has moved from an angle of zero (if aligned with axis 212) to a second position 214 having an angle $\Theta$ equal to 10°. At this angle, emission data intensity values are shown in graph 206a. The corresponding sinogram 204a is shown as partially constructed for the emission values for each detector pixel position for the angles between 0 and 10°. FIG. 2B illustrates a second orientation 202*b* for the detector 211 and sample at an angle Θ equal to 84° (between 216 and 212) with a corresponding emissions 206*b* and sinogram 204*b*. FIG. 2C illustrates a second orientation 202*c* for the detector 211 and sample at an angle Θ equal to 180° (between 218 and 212) with a corresponding emissions 206*c* and sinogram 204*c*.

Figure 2D:
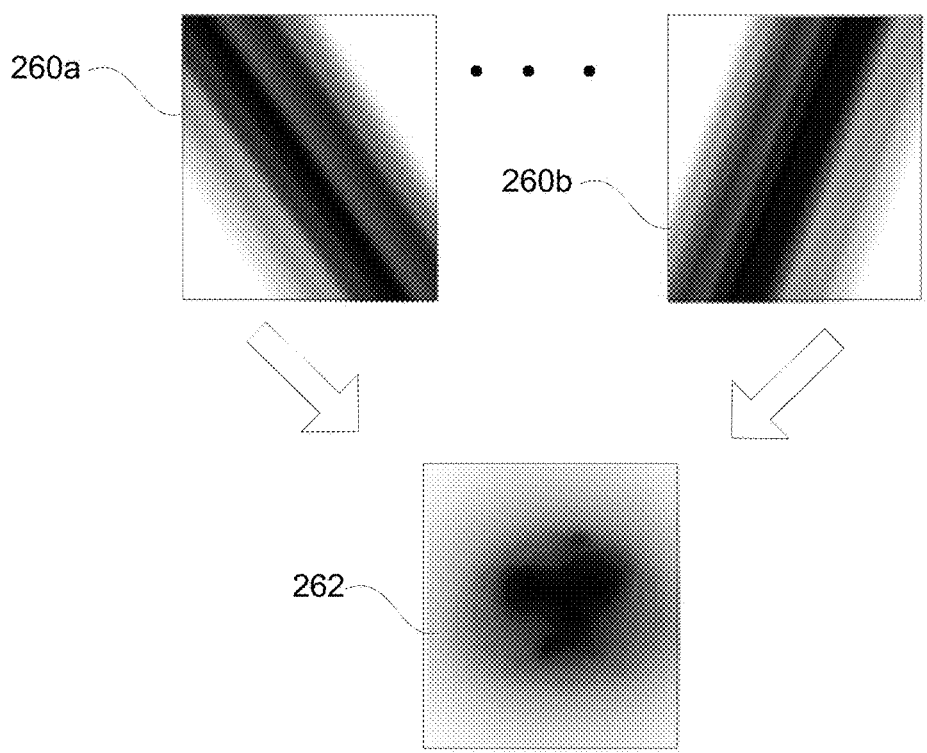

The data from the sinogram can then be back projected to obtain a reconstructed image. FIG. 2D illustrates how the sinogram data from all of the angles is back projected into the same image space. In general, back projection is a process in which the measured profile associated with each specific angle of acquisition is "smeared" across the image space to form a back projected image. For instance, the sinogram data for angle of 45° may be back projected to form back projected image 260*a*, while the sinogram data for angle 120° is used to form back projected image 206*b*. The sinogram data at all the angles (only two angles are illustrated) are used to form back projected images that are overlaid to generate the final reconstructed image 262.

For an image reconstruction based on a sinogram to effectively produce an accurate image, the center of the image is expected to lie on the line between the radiation center (spot) and a vertical line centered on the horizontal midpoint of the detector. When the rotational axis is not centered, the sinogram image (the overlay image of all images) turns out blurry and cannot be used to identify key features for the resulting reconstructed image.

Figure 3:
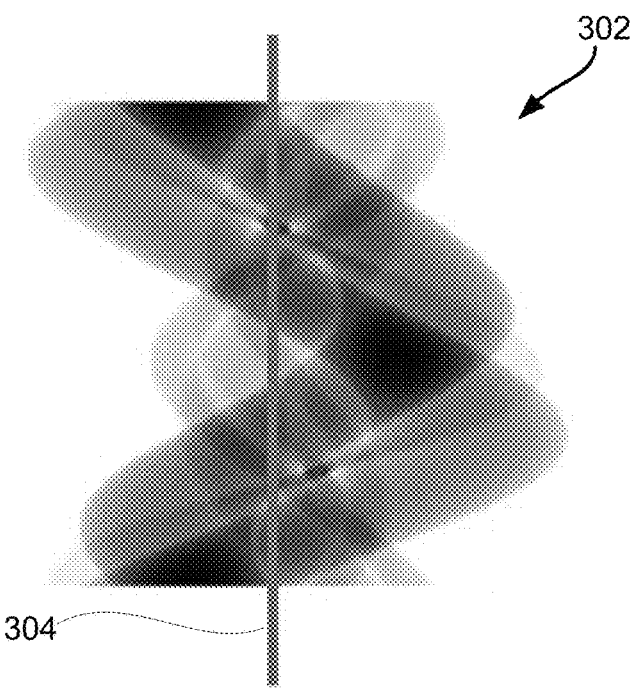
FIG. 3 illustrates a balancing process for determining a center line correction from a sinogram.

FIG. 3 illustrates a balancing process for determining a center line correction 304 from the sinogram 302. This line of balance 304 is typically found by adding the grayscale values of the pixels on each side of the line to obtain a grayscale value total for each side, and then moving the line until each side has an equal grayscale value total. However, this balancing technique is not reliable due to various issues, e.g., variable output from the X-ray tubes.

Figure 4A:
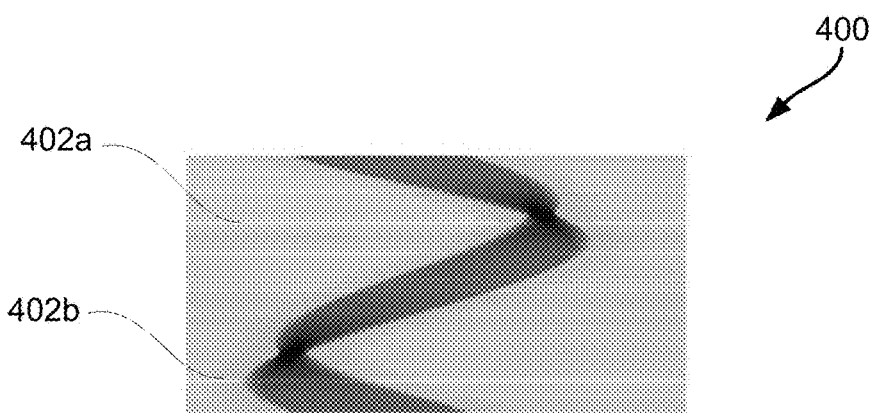
FIG. 4A illustrates variable x-ray tube output that results in white lines across the sinogram image.
Figure 4B:
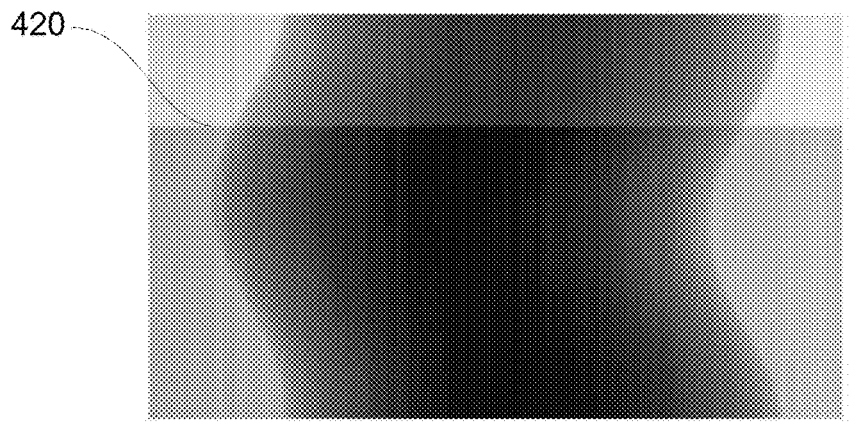
FIG. 4B also illustrates another example inconsistent grayscale values in the sinogram that is caused by a common tube output variation.

FIG. 4A illustrates variable x-ray tube output that results in white lines, such as 402*a* and 402*b*, across the sinogram image 400. FIG. 4B also illustrates another example of inconsistent grayscale values in the sinogram that are caused by a common tube output variation. As shown, the sinogram image contains a horizontal line 420 caused by variable x-ray tube output.

Figure 4C:
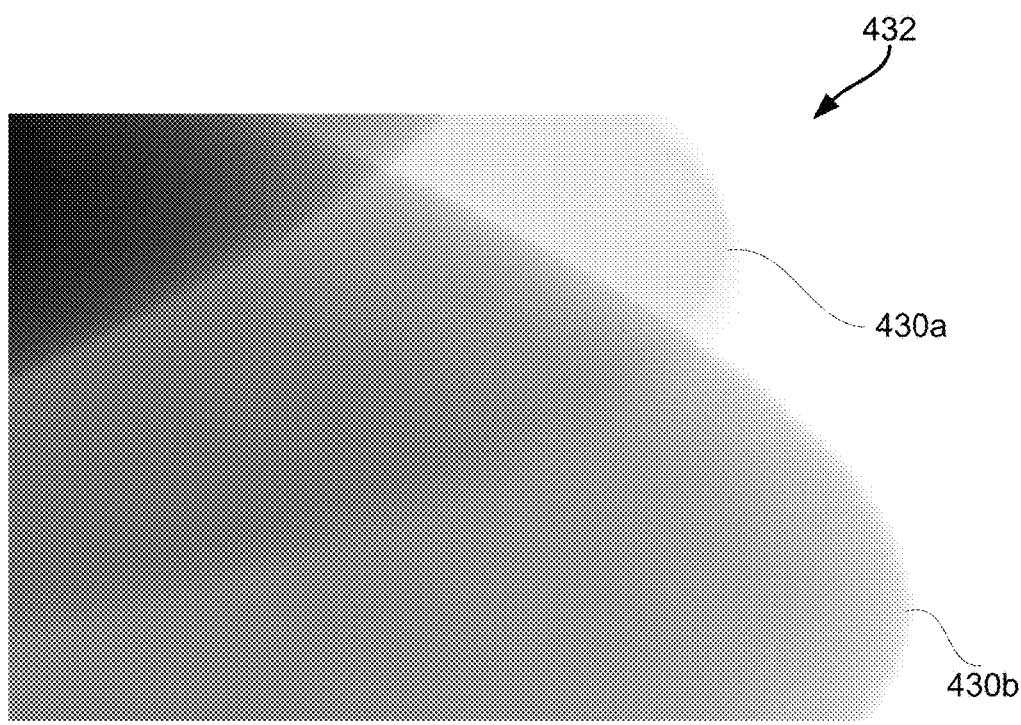
FIG. 4C illustrates two peaks on the right side of sinogram for determining a center line for such sinogram.
Figure 4D:
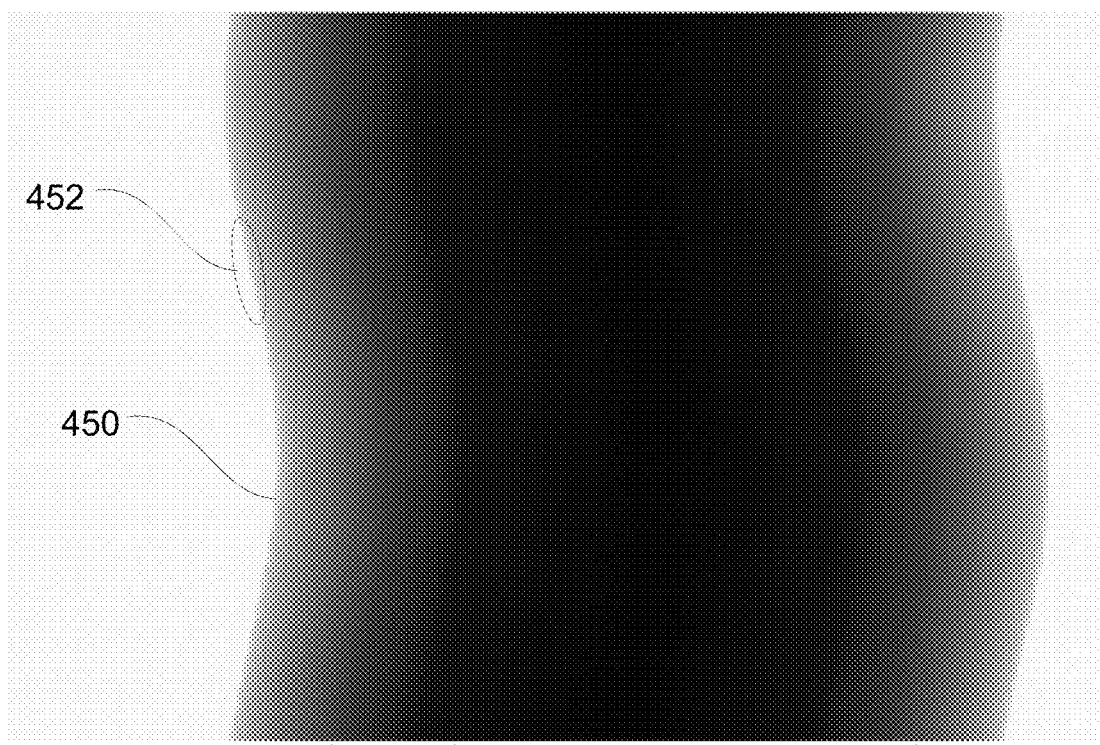
FIG. 4D illustrates another form of sinogram edges that are not defined well for determining a center line for such sinogram.

There are numerous issues with a typical sinogram that may make it difficult to determine the center line. For instance, the software for finding a line of balance may look for the peaks of the sinogram to determine the center line as being positioned between peaks on each side of the sinogram. FIG. 4C illustrates two peaks 430*a* and 430*b* on the right side of sinogram 432 for determining a center line for such sinogram. As can be seen, these peaks are not very defined and their positions would be difficult to determine accurately and, hence, may likely cause an inaccurate center line determination. FIG. 4D illustrates another form of sinogram edges that are not defined well for determining a center line for such sinogram. In this example, the sinogram edge 450 can be seen to be formed from a gradual fade from the imaged structure's dark intensity to the background field's white intensity (e.g., region 452).

Figure 5A:
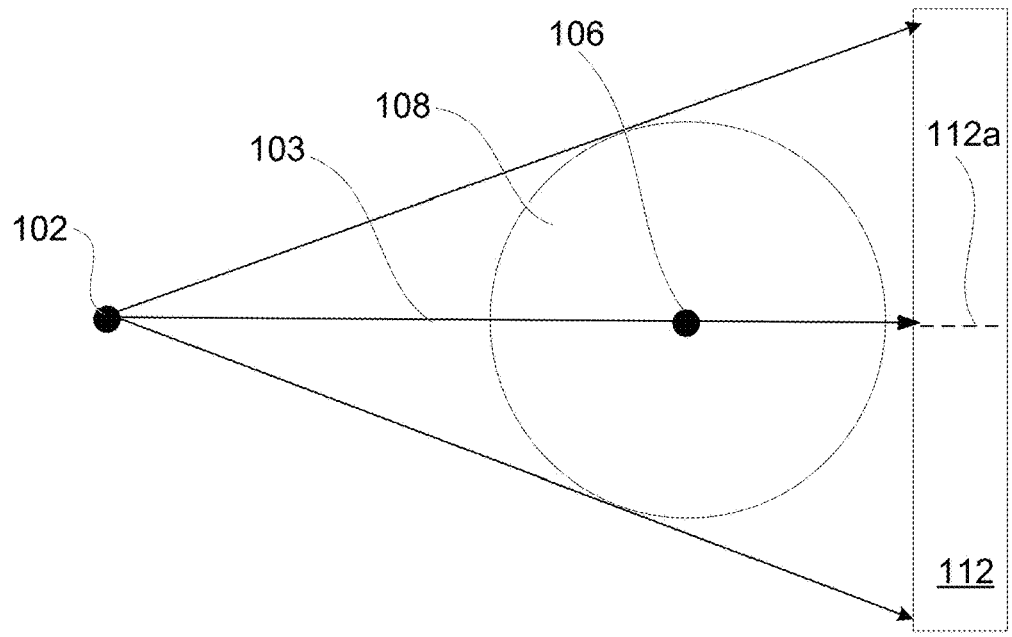
FIG. 5A illustrates rotation of the specimen when perfectly centered.

FIG. 5A illustrates rotation of the specimen table 108 when it is perfectly centered with respect to the center of radiation (e.g., 102). As shown, the axis of rotation 106 of the specimen 108 is centered so that a center line 103 from the center spot of the origin of radiation 102 runs through both the axis of rotation 106 and the center of the detector face.

Under various conditions, the sample may be off center in its rotation relative to the detected projections, and this off-centered aspect of the rotating sample support table detrimentally affects the reconstructed image results. For example, the mechanical moving parts of the rotating support on which the sample is placed may be slightly out of alignment so that the center of rotation is offset from its expected position. An off-center amount that is even as low as $5/1000^{th}$ of an inch may eliminate usefulness of the CT scan data.

Figure 5B:
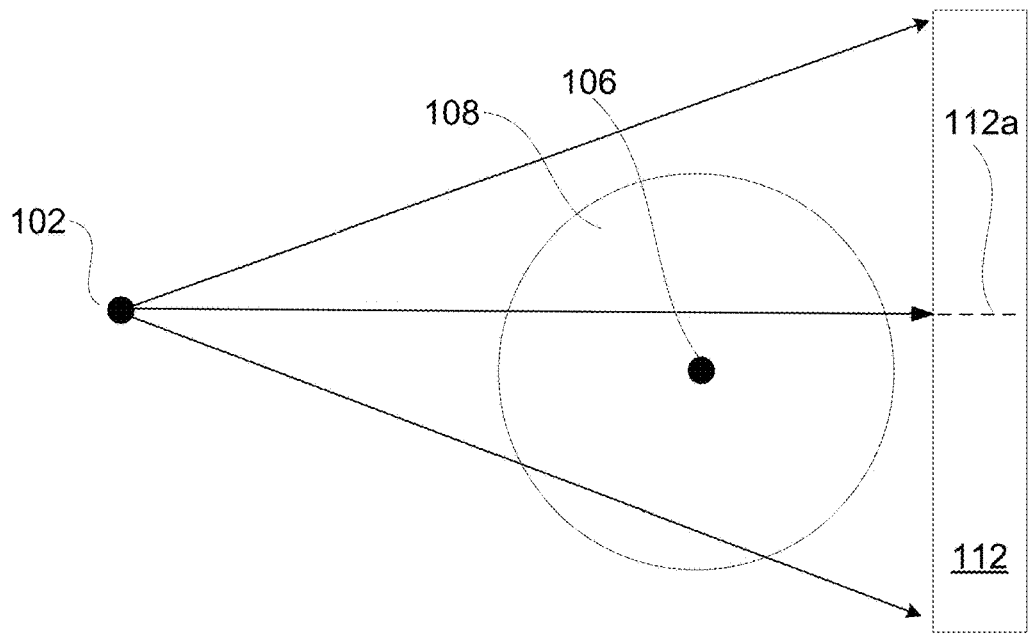
FIG. 5B illustrates rotation of the specimen when off centered.
Figure 5C:
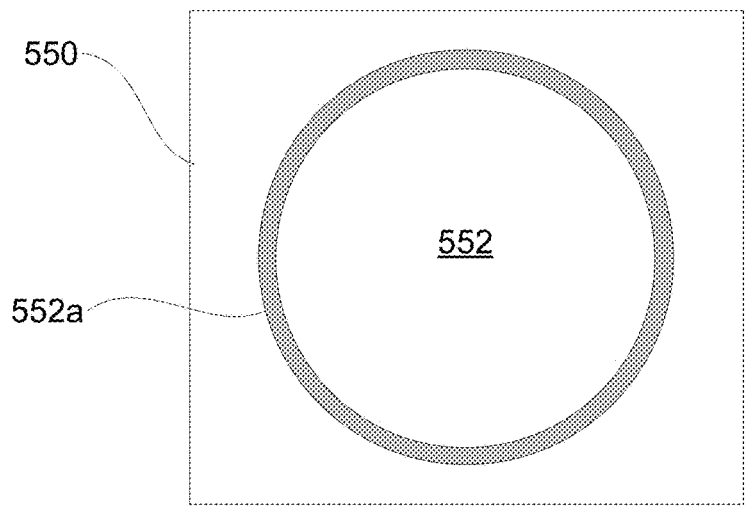
FIG. 5C is a diagrammatic representation of the imaging results from an off-center specimen in the form of an aluminum disk.

FIG. 5B illustrates rotation of the specimen when it is off center with respect to the focal point of the rays of attenuated radiation. As shown, the sample table 108 has a center of rotation 106 that is off center from the center of the radiation spot 103. FIG. 5C is a diagrammatic representation of the imaging results for an aluminum disk sample. As illustrated, the image 550 includes a pixelated specimen image 552 having a noticeably blurred edge 552*a* due to the off-center portion of the specimen. When an object is not centered, the sinogram image (the overlay image of all images) turns out blurry and cannot be used to readily identify key features (e.g., along the specimen edge). Additionally, magnification increases the effect of blurriness so that analysis of the image becomes increasingly more difficult. A defect may be difficult to see anywhere on the image.

Figure 6:
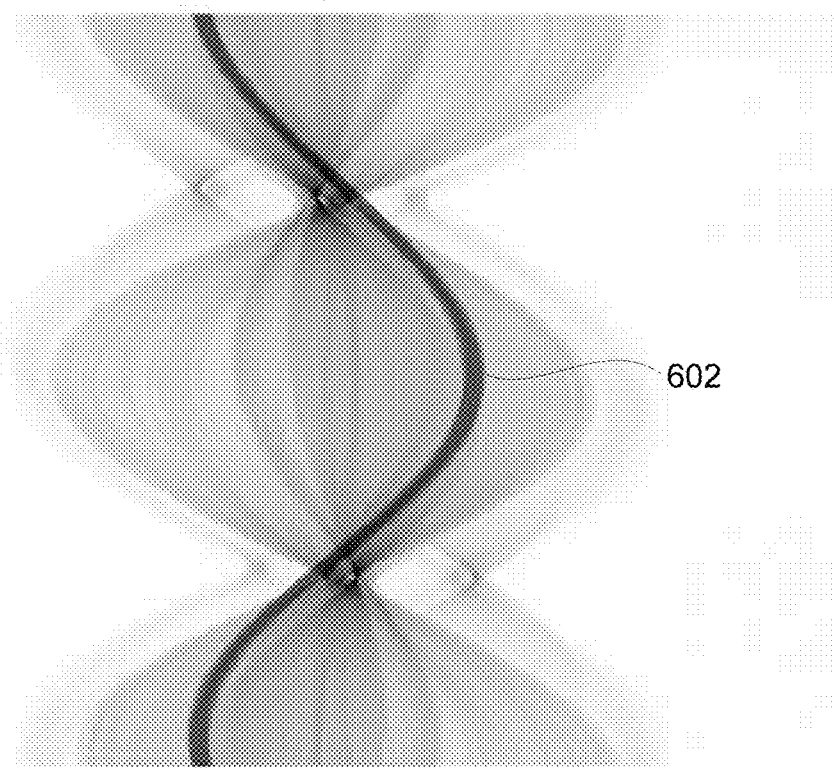
FIG. 6 illustrates a sinogram image that results from scanning a low density wire that has been added to a scanned round object.

The projections (images) can be properly aligned if a system/engineer knows the offset amount of the object being scanned. However, determining which aspects of the image (e.g., sinogram image) are due to offset vs. geometry is difficult for both computers and people. In one solution, a wire is attached to a low density object that is being imaged. The wire theoretically shows up in the sinogram to facilitate determination of the center line of such sinogram. However, as shown in FIG. 6, there is a gradual fade to white along the imaged wire's edge (e.g., 602) in the sinogram image. In certain cases, the high density wire will lower the image quality because the lower density object being scanned will "wash-out" or fade in the final slice image because the range of grayscale-values for the object will be greatly reduced due to the bandwidth of the image being consumed by the need to display the high density image.

Figure 7A:
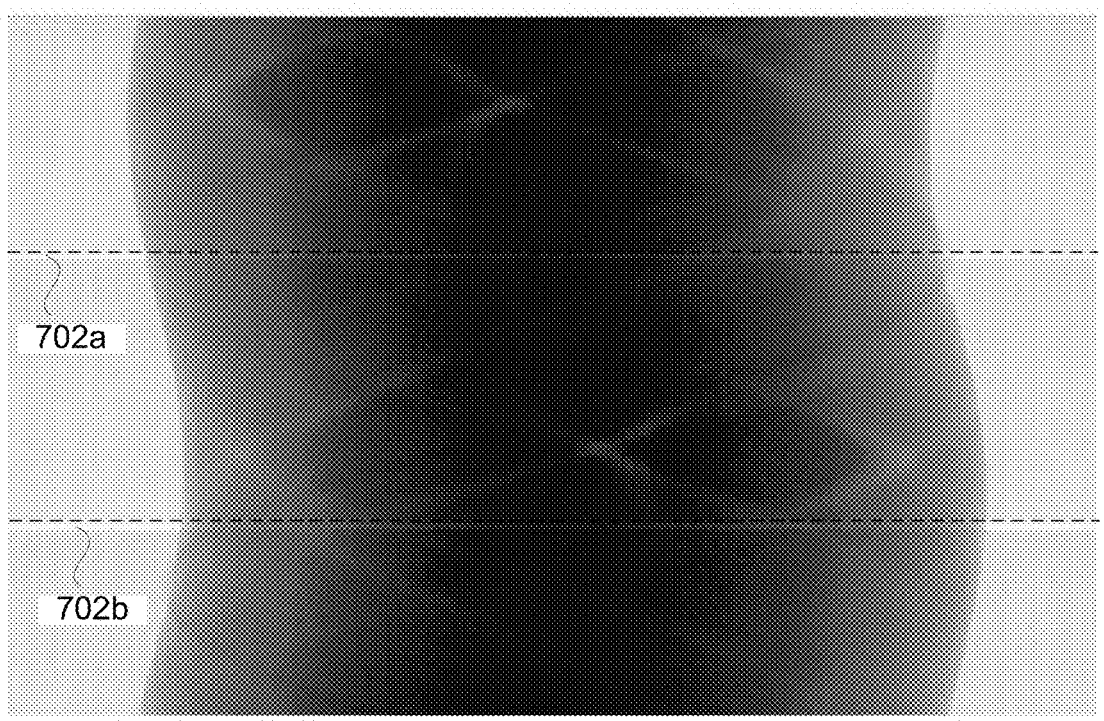
FIG. 7A represents a sinogram image for a composite disk.
Figure 7B:
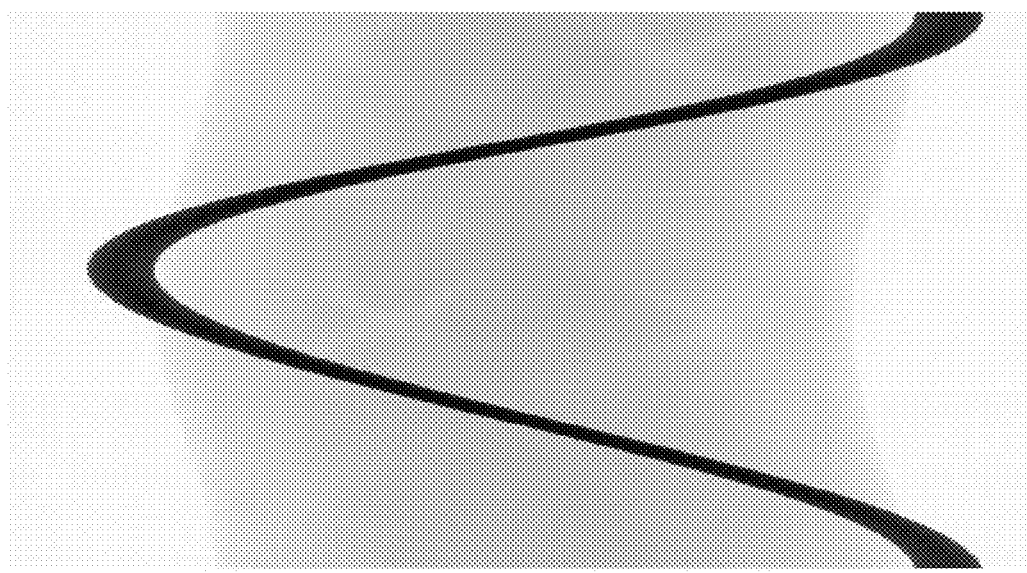
FIG. 7B illustrates a sinogram image of the composite disk of FIG. 7A with the addition of a wire object.

FIG. 7A represents a sinogram image for a composite (e.g. fiberglass) disk or "puck." The resulting sinogram image shows part features, which are to be analyzed for defects, but may be difficult to distinguish within the disk's resulting sinogram image. One issue that may make it difficult to reconstruct an accurate image is the white lines 702*a* and 702*b* due to the tube variation, which may cause inaccurate determination of the center line for such sinogram. Addition of a wire object around the puck of FIG. 7A does not provide an acceptable solution as seen in the resulting sinogram of FIG. 7B. As illustrated, the wire causes the object's features to fade and become indistinguishable due to contrast issues.

Figure 8A:
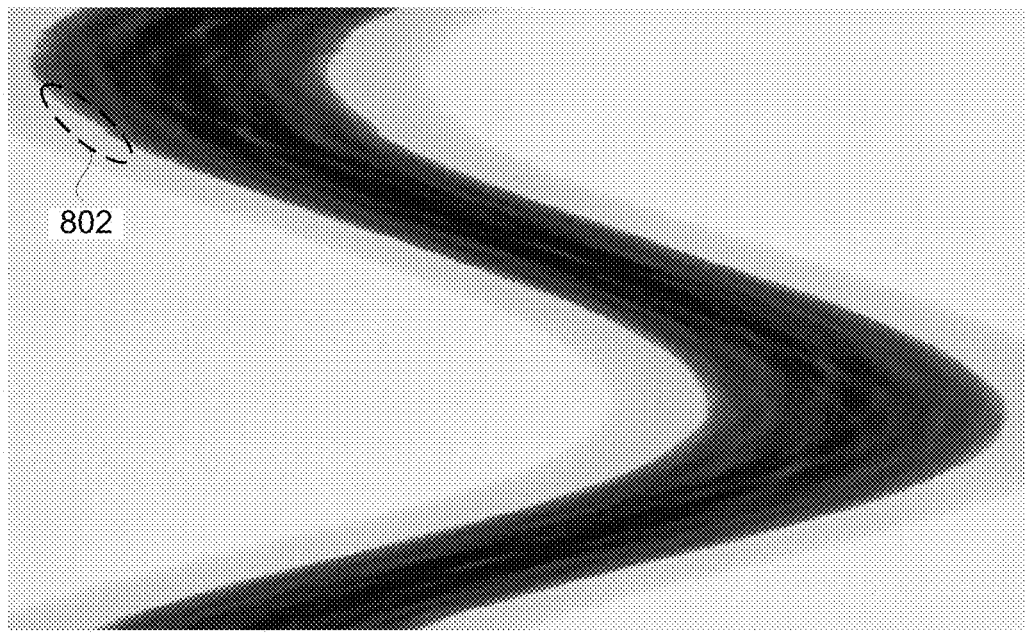
FIG. 8A illustrates rough edges in a sinogram image.
Figure 8B:
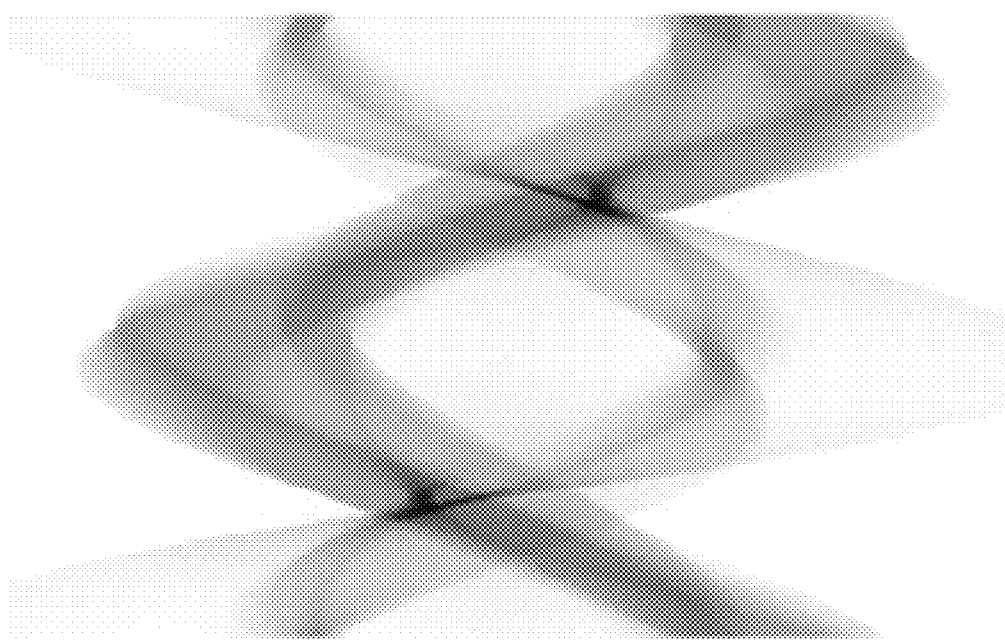
FIG. 8B illustrates a sinogram having minimal contrast.

There are numerous issues that can adversely affect the sinogram image. FIG. 8A illustrates rough edges (e.g., region 802) in a sinogram image. The positions of these rough edges would be difficult to use to calculate the center line for such sinogram. FIG. 8B illustrates a sinogram having minimal contrast, which also makes it difficult to determine a center line for such sinogram.

Figure 8C:
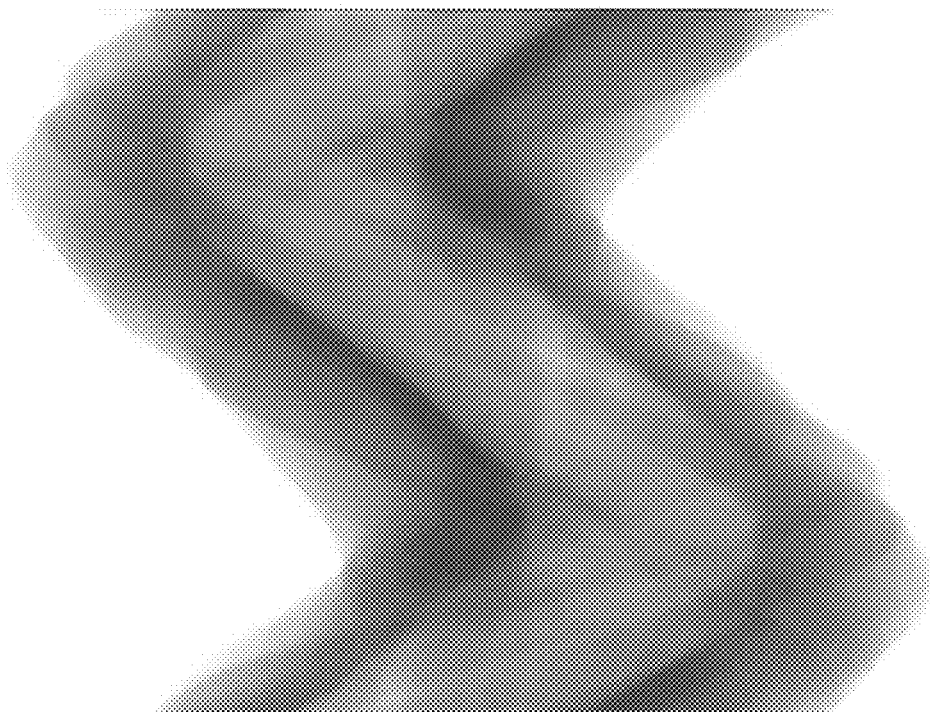
FIG. 8C illustrates another sinogram image for which it is difficult to determine a center line due to sinogram edges that are not clearly defined.
Figure 8D:
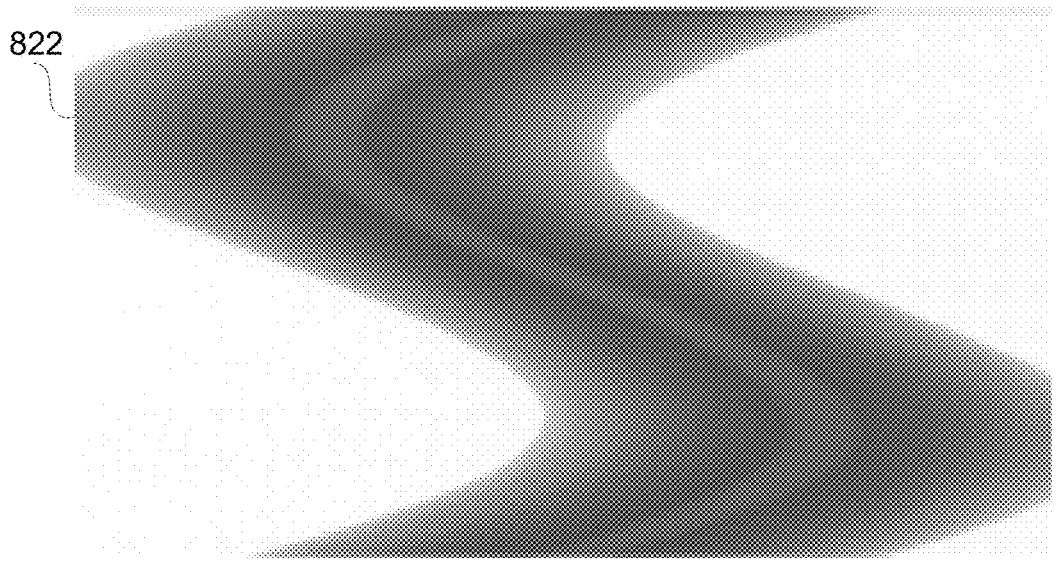
FIG. 8D illustrates a sinogram that is generated when the part being scanned moves out of range of the detector.

FIG. 8C illustrates another sinogram image for which it is difficult to determine a center line due to sinogram edges that are not clearly defined. FIG. 8D illustrates a sinogram that is generated when the part being scanned moves out of range of the detector, resulting in part of the object image being cut off (e.g., region 822). The resulting sinogram is not balanced due to cutoff edges, making it difficult to determine an accurate center line.

Center Calibration Indicator and Use Embodiments

Figure 9A:
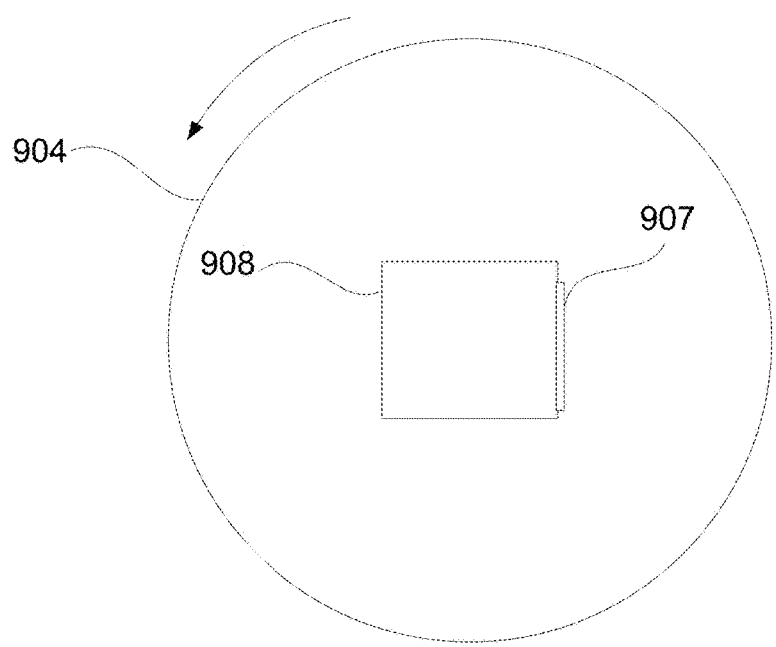
FIG. 9A is a diagrammatic top view representation of a center calibration indicator (CCI) adjacent to an object undergoing a CT image scan in accordance with one embodiment of the present invention.

Certain embodiments of the present invention provide mechanisms for facilitating an accurate determination of the center offset and allowing the use of CT scans on parts with varying symmetry, thickness, features and densities. In certain embodiments, an object of specific geometry and density is placed in the vicinity of the object being scanned. The object of specific geometry and density is referred to as a Center Calibration Indicator (CCI). FIG. 9A is a diagrammatic top view representation of a CCI adjacent to an object undergoing a CT image scan in accordance with one embodiment of the present invention. In this example, the CCI is in the form of a thin rectangular object 907 of material chosen based on the material of the part being scanned. As shown, the CCI 907 is affixed to a side of the object 908 that is positioned on a rotating turntable 904 while being scanned.

Figure 9B:
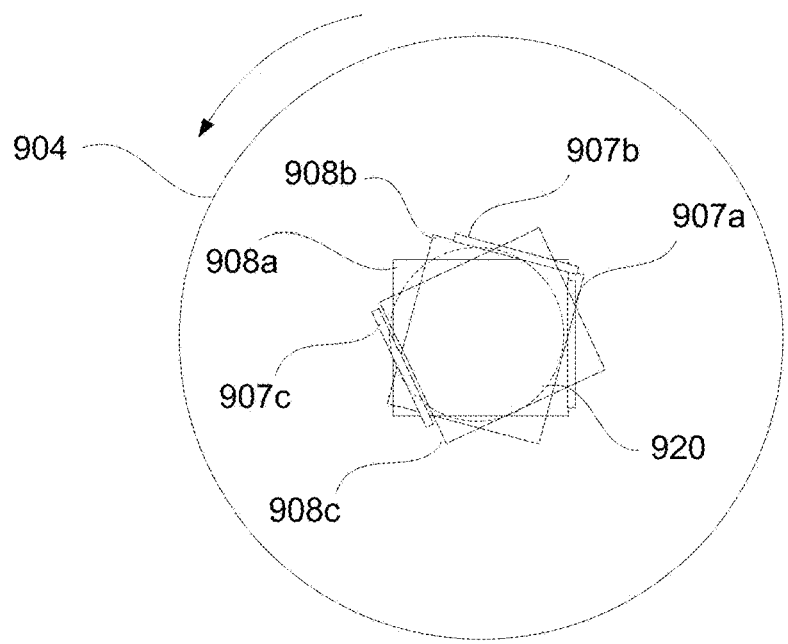
FIG. 9B shows rotation of the turn table, along with the object and CCI, of FIG. 9A in accordance with one implementation of the present invention.

FIG. 9B shows rotation of the turn table 904, along with the object and CCI, in accordance with one implementation of the present invention. As the object and associated CCI rotate with respect to the detector, the CCI pixel density, which is captured in a sinogram image, varies. By using the point where the CCI pixel density is highest (e.g., when the CCI face plane is perpendicular to the CT scan plane), the precise offset for the CCI and the nearby part that is being imaged can be calculated as further described below. In FIG. 9B, the object 908a and CCI 907a are shown at a first rotation position, and the object 908b and CCI 907b are shown at a second rotation position. The object 908c and CCI 907c are then shown at a third rotation position. In general, the object and CCI follow a circular path.

Figure 10:
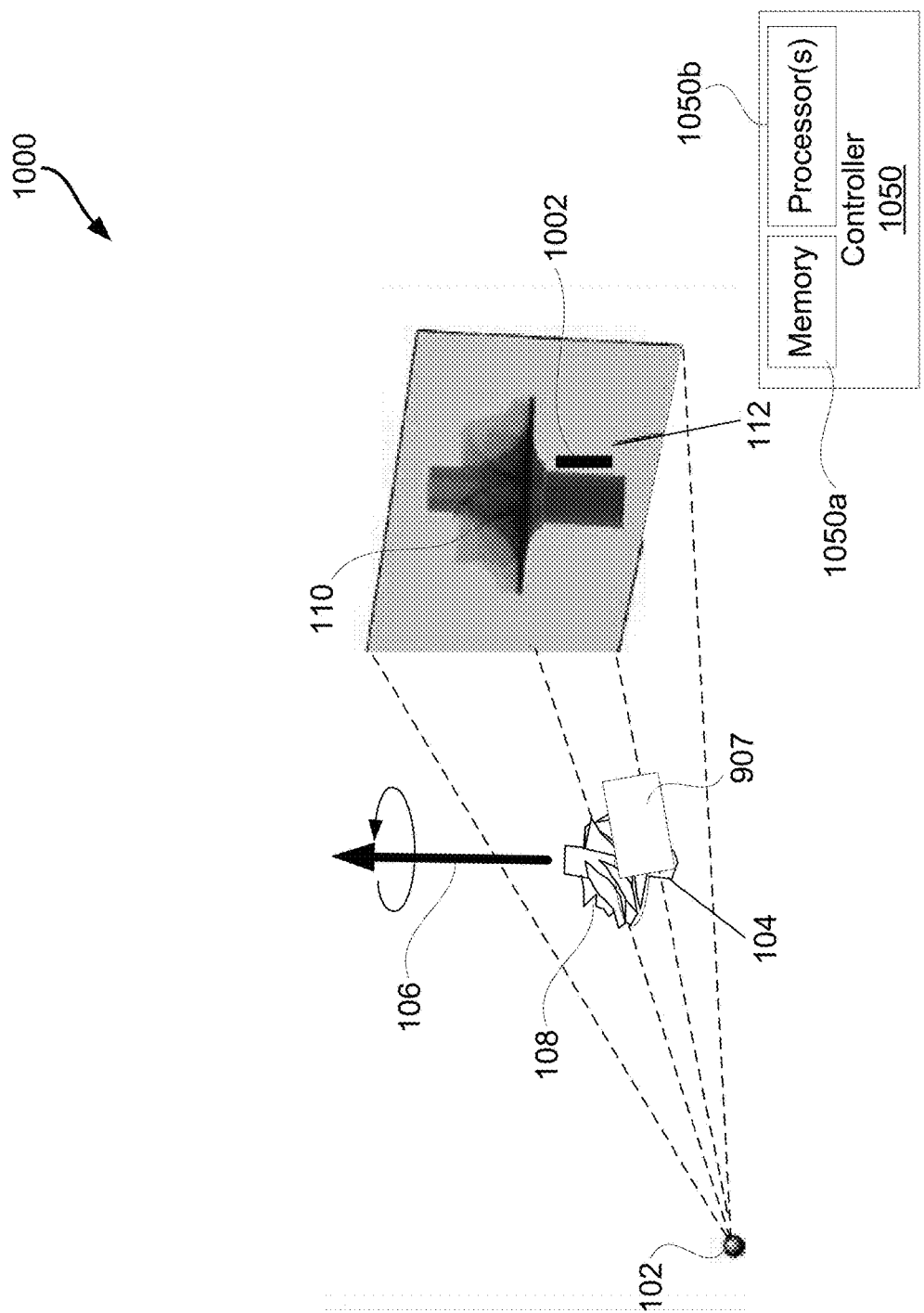
FIG. 10 is a diagrammatic representation of a CT imaging system set up in accordance with a specific application of the present invention.

FIG. 10 is a diagrammatic representation of a CT imaging system set up 1000 in accordance with a specific application of the present invention. This imaging system 1000 has similar components, which are identically labeled, as the system illustrated in FIG. 1. As shown for this set up 1000, a CCI 907 is affixed with respect to the object 108 being scanned. As shown, a CCI image 1002 is present alongside the object image 110.

The support (specimen and CCI) may be rotated respect to the detector and/or the detector rotated relative to the specimen by any suitable mechanism so as to scan different angles of the specimen. For example, a motor mechanism may be utilized to rotate the support.

The CT imaging system 1000 may also include one or more controllers (e.g., 1050) for controlling the components of the system 1000 and processing projection data in accordance with techniques of the present invention. The projection data captured by the detectors can be processed by controller 1050 or, more generally, by one or more signal processing devices, which may each include an analog-to-digital converter configured to convert analog signals from each sensor into digital signals for processing. The controller 1050 typically has one or more processors (1050b) coupled to input/output ports, and one or more memories (1050a) via appropriate buses or other communication mechanisms.

The controller 1050 may also be in the form of a computer system that includes one or more input devices (e.g., a keyboard, mouse, joystick) for providing user input, such as changing focus and other inspection recipe parameters. The controller 1050 may also be connected to the support for controlling, for example, a specimen position and connected to other system components for controlling other imaging parameters and configurations of such system components.

The controller 1050 may be configured (e.g., with programming instructions) to provide a user interface (e.g., a computer screen) for displaying data, such as projection data, sinogram images, and resulting specimen image. The controller 1050 may be configured to analyze such images for defects. The controller 1050 may be configured (e.g., with programming instructions) to provide a user interface (e.g., on a computer screen) for displaying data, images, and analysis results. In certain embodiments, the controller 1050 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 11A:
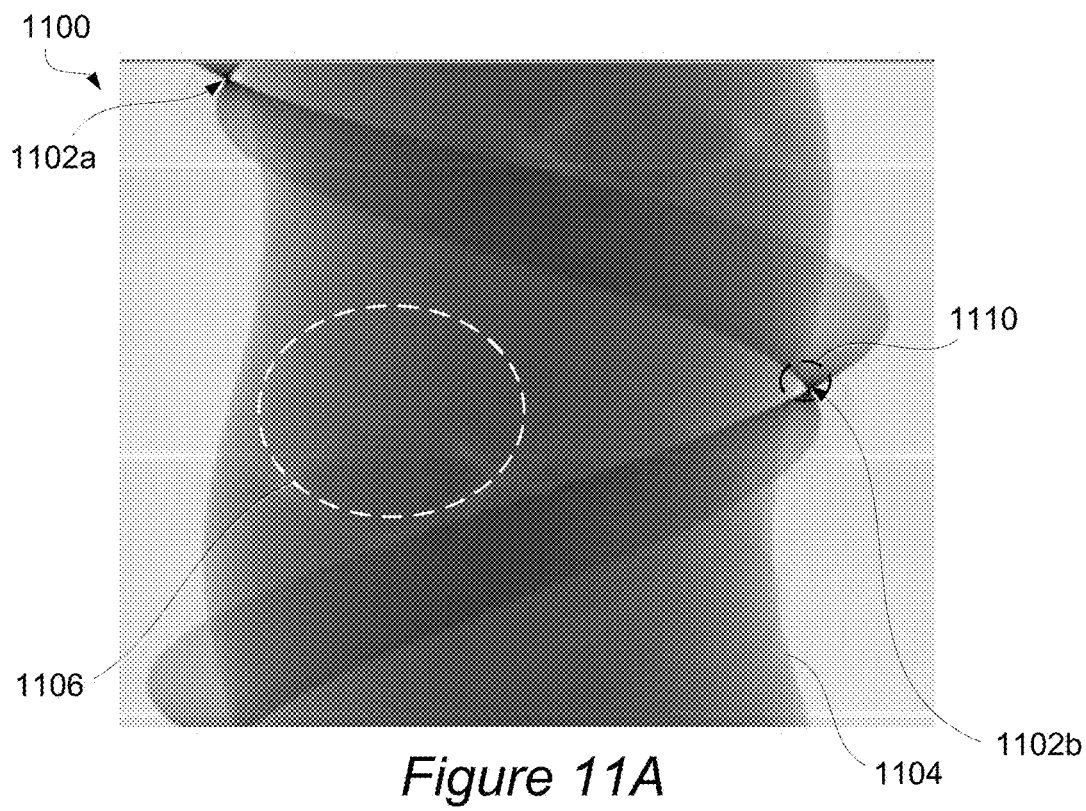
FIGS. 11A and 11B illustrate use of a CCI to facilitate center offset determination in accordance with one embodiment of the present invention.
Figure 11B:
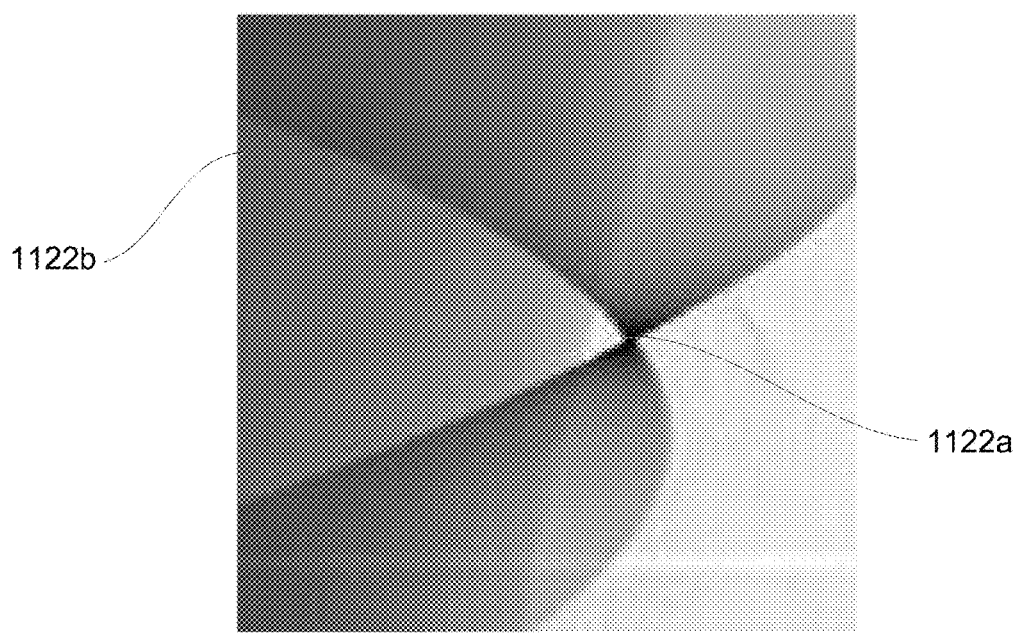

FIGS. 11A and 11B illustrate use of a CCI to facilitate center offset determination in accordance with one embodiment of the present invention. As shown, the CCI is sized and shaped so that two distinct alignment points (1102a and 1102b) are clearly visible in the sinogram image 1100 as seen in FIG. 11A. These alignment points can be used to determine a center offset as described here, by way of examples. On the other hand, the feature being scanned results in low contrast edges (e.g., 1104), which gradually fade to white, and featureless areas (e.g., 1106) in the sinogram that are not useful for center offset determination. The midpoint between the alignment points represent the center of rotation. When this location is compared to the midpoint of the image, the difference is the offset to the image center at magnification. When this distance is divided by the magnification, the true offset error is found. Magnification is the distance from the spot to the detector divided by the distance from the spot to the center of rotation of the specimen table.

The relative attenuation between the object-under-test, and the CCI can be designed to ease a process for locating the alignment points from the CCI. Increasing the length of the CCI can be selected to result in significant sinogram contrast between CCI-based alignment points (e.g., 1122a) and the object being scanned 1122b, as shown in FIG. 11B.

Figure 12A:
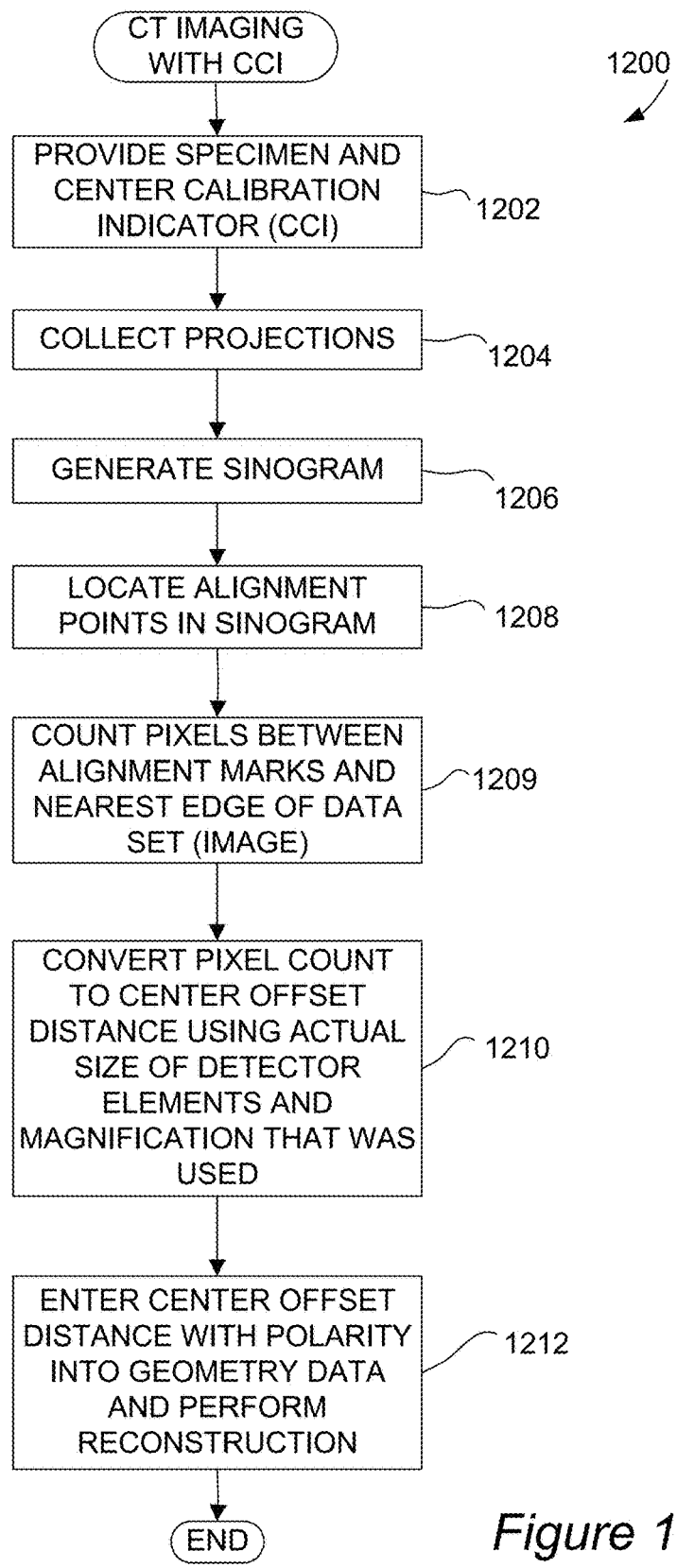
FIG. 12A is a flow chart illustrating a procedure for determining a center offset for a CT scan in accordance with a specific embodiment of the present invention.

Any suitable technique may be used to determine a center offset for a rotating sample undergoing a CT scan. FIG. 12A is a flow chart illustrating a procedure 1200 for determining a center offset for a CT scan in accordance with a specific embodiment of the present invention. Initially, a specimen and CCI are provided in operation 1202. Any suitable CCI may be used and positioned in any suitable position so that the CT scan enables an accurate center offset determination. In one embodiment, a CCI results in two opposing points of contrast that accurately depict the offset distance and are locatable positions (e.g., sharp, clear points) equidistance from the center line in the sinogram.

The material of the CCI may be chosen so that the image of the CCI has a significant contrast with the object under test. For instance, the density of the CCI may be selected to differ from the object being scanned by at least 25%, or even at least 50%.

The CCI may be designed to have a rectangular cross section with minimal thickness and a length that has been found to cause a marked decrease in grey level values at points during rotation of the part during the scan. The points occur when the rectangle is positioned perpendicular to the detector so that the emissions traverse through a significantly larger path in the CCI, as compared to other positions. That is, a portion of the radiation from the spot to the portion of the detector used to create the sinogram passes through the entire length of the CCI. The thickness is minimal, to minimize attenuation when the CCI is out of alignment.

Figure 12B:
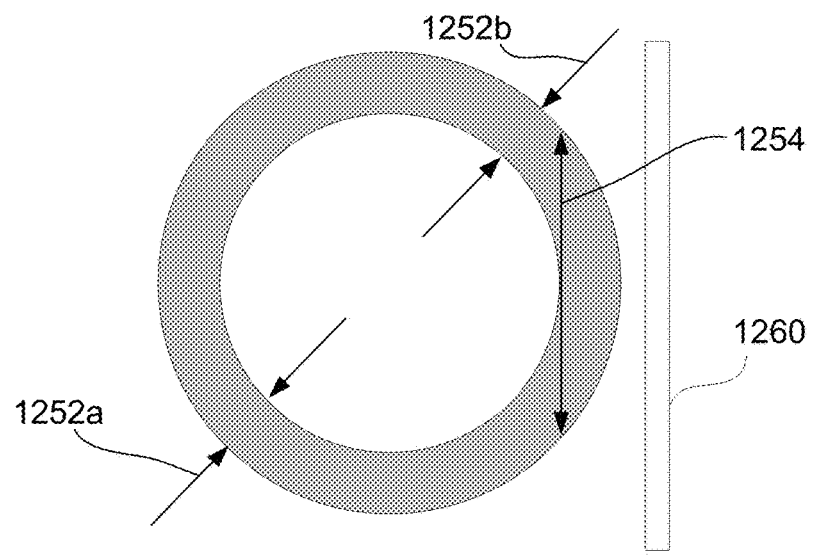
FIG. 12B is a diagrammatic representation of rays traveling through different sized paths through the object under test and the CCI in accordance with one embodiment of the present invention.

When an object is scanned, the rays of radiation travel through the part. Often, the rays have to follow a path much longer than a measured thickness. FIG. 12B is a diagrammatic representation of rays traveling through different sized paths through the object under test and the CCI in accordance with one embodiment of the present invention. As shown, the object under test is a hollow tube with many path lengths through which the rays can travel as the object rotates. For instance, rays can travel through the object's thickness two times, e.g., 1252a and 1252b, or through a longer path 1254. The longer distanced path 1254 will cause more attenuation in the projection that is aligned with this path.

Figure 12C:
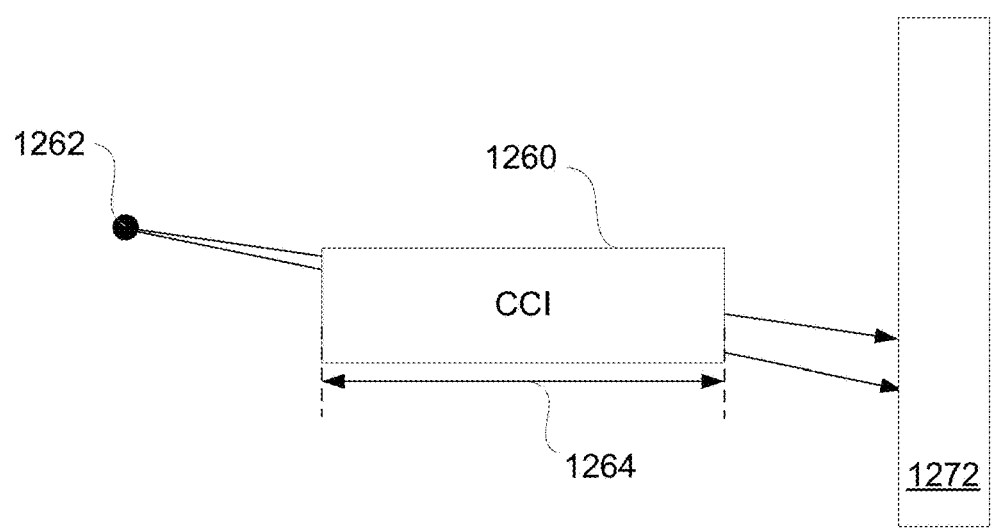
FIG. 12C illustrates a CCI that is sized so that the rays pass through the entire CCI length in accordance with one implementation of the present invention.

The CCI is preferably designed so that it has at least two projection paths that are longer than the longest path going through the object under test. As shown in FIG. 12B, CCI 1260 has a length that is longer than the longest path 1254 through the object under test. FIG. 12C illustrates a CCI that is sized so that the rays pass through the entire CCI length in accordance with one implementation of the present invention. As shown, the rays emitted from source 1262 pass through the full length 1264 of CCI 1260 onto detector 1272. This CCI design will provide the greatest attenuation among all of the projections. In preferred embodiments, the CCI has at least two faces that have a minimal and uncurved or straight-edge profile when rotated to two positions that are aligned with two opposite sides of the detector. For example, two opposite faces of the rectangular shaped volume have a thin elongated rectangular shape or thin profile, while two other other opposite sides of the volume (that will also be rotated to face the detector) have a significantly larger area than the thin profile's area. The thin profile sides are preferably not curved and do not present a curved profile or edge, and such design tends to allow the corresponding points to show up at symmetrical positions in the resulting sinogram image. This design will also make the points that correspond to the CCI more readily identifiable in the sinogram.

The CCI may be affixed adjacent to the specimen by any suitable attachment components, such as tape, glue, one or more fastener(s) (bolt, screw, nail, etc.), etc. The position of the CCI relative to the specimen is such that the scanned field of view for obtaining the projections of the specimen also includes the CCI. In one example, the CCI is positioned such that the radiation travels from the spot to the center of the detector. In another example the CCI is placed above or below this center of the detector. This second location may be chosen for a variety of reasons. In general, the sinogram is created from data collected where the rays through the CCI impinge on the detector.

After the CCI is set up, the projections of the specimen and CCI may then be collected in operation 1204. In one embodiment, the specimen is rotated relative to a detector. In alternative embodiments, the detector is rotated relative to the specimen. The scan may be any suitable type of imaging that requires multiple projections and image reconstruction. Example scanning technologies that may utilize a CCI include CT, any type of positron emission, any single positron computed tomography (SPEC), etc.

A sinogram may then be created based on the collected projection data in operation 1206. Example techniques for forming a sinogram based on projections of collected emissions at different rotational angles are further described below. After the sinogram is formed, the alignment points in the sinogram, which were caused by the CCI, may then be located in operation 1208. For instance, the sharp points (e.g., 1102a and 1102b) from the CCI in the sinogram may be located. For instance, these locations may be located because they are the most attenuated points on the sinogram.

Any suitable technique may then be used to determine the center offset based on image features corresponding to the CCI. As shown, the pixels between the alignment marks and the nearest edge of the data set (or image) may be counted in operation 1209. That is, the number of pixels between each alignment point and the image edge is determined. The pixel count may then be converted to a center offset distance using the actual size of the detector and magnification that was used in operation 1210. For instance, the distance between each alignment point and the image edge is determined and the two distances are compared to determine a final offset and polarity. The difference will be zero if the center of the sinogram is equal distance to the two alignment marks (e.g. the two alignment points are equal distance to the nearest image edge). Said in another way, the center of the image can be compared to the midway point between the alignment marks, accounting for detection size and magnification, as described above The actual offset of center of rotation and the center of the detector can be determined based on the detector element size (or pixel size) and accounting for the magnification. This technique yields an offset that is based on multiples of the detector element size (or pixel size). Alternatively, the offset may be determined to be a fraction of the detector element size (or pixel size). Any suitable technique may be used to determine an offset that is a fraction of detector element size. For instance, the actual offset may be based on the projection angular position and/or neighbor pixels.

Figure 12D:
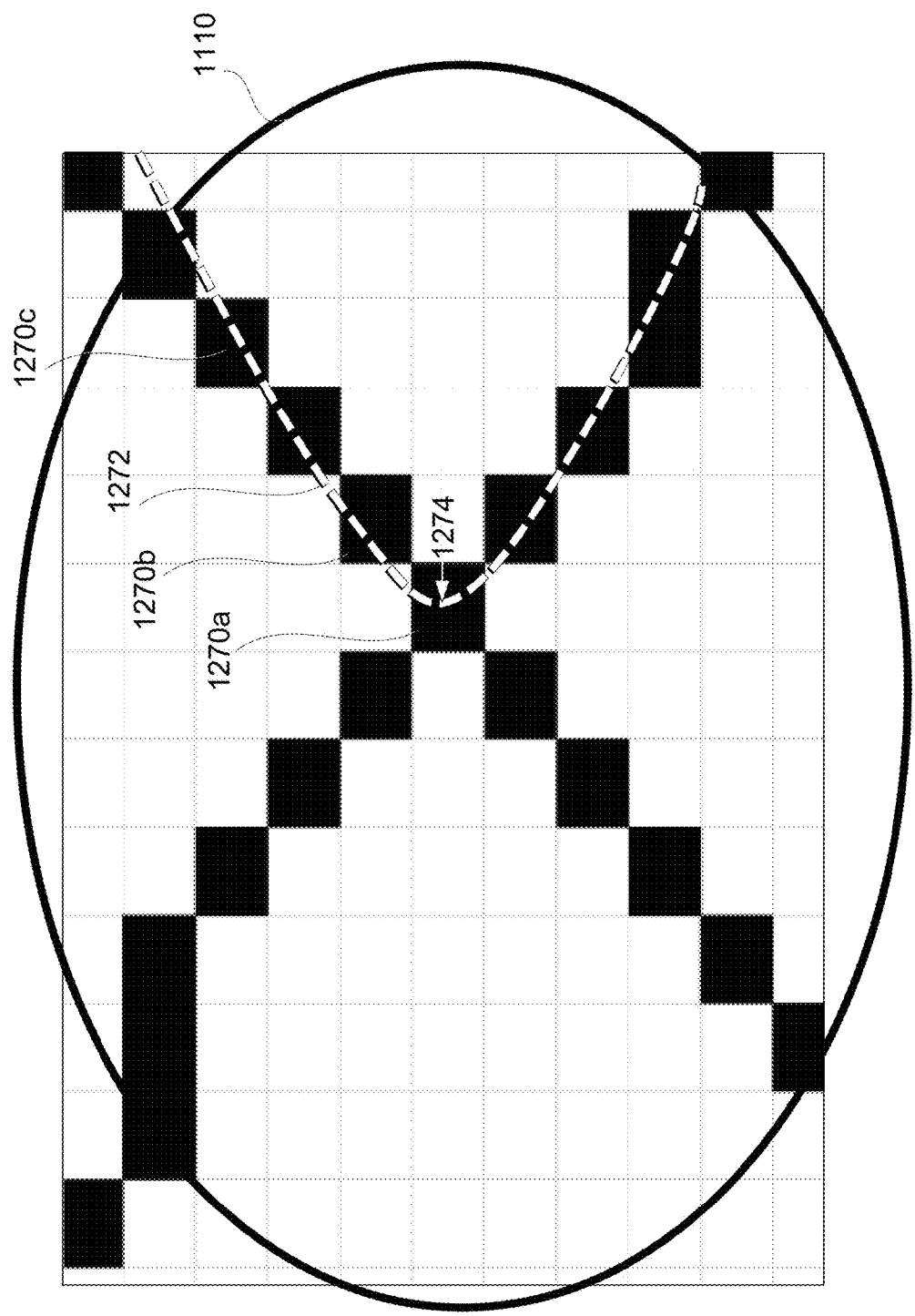
FIG. 12D is a diagrammatic representation of a technique for determining a center offset using a fraction of a pixel in accordance with an alternative embodiment of the present invention.

FIG. 12D is a diagrammatic representation of a technique for determining a center offset using a fraction of a pixel within the sinogram in accordance with an alternative embodiment of the present invention. As shown, the highest attenuation pixels (such as pixels 1270a, 1270b, 1270c) for the CCI can be located in the resulting sinogram. For instance, the sinogram portion 1110 with the highest attenuation pixels shown in FIG. 12D corresponds to the sinogram portion 1110 of FIG. 11A. A curve 1172 can be fitted to these pixels so that such curve 1172 represents an edge of the CCI that has been mathematically interpolated to be a smooth continuous edge. The position of the peak 1274 of this curve 1272 can be defined as one of the alignment points. In this example, peak's position is determined to be within the voxel/pixel 1270a, as opposed to at the edge of such pixel. This process can be repeated on the other alignment point. The two alignment point positions can then be used to determine the offset as described further herein.

Referring back to FIG. 12A, the offset distance with the polarity may then be entered into the geometry data (e.g., that was used in the sinogram) and image reconstruction performed in operation 1212. For instance, reconstruction may then be performed to produce a high quality image with no blurring due to an inaccurate center offset. The procedure then ends. However, this process 1200 may be repeated for any number of sub-portions and positions of the specimen.

Figure 13:
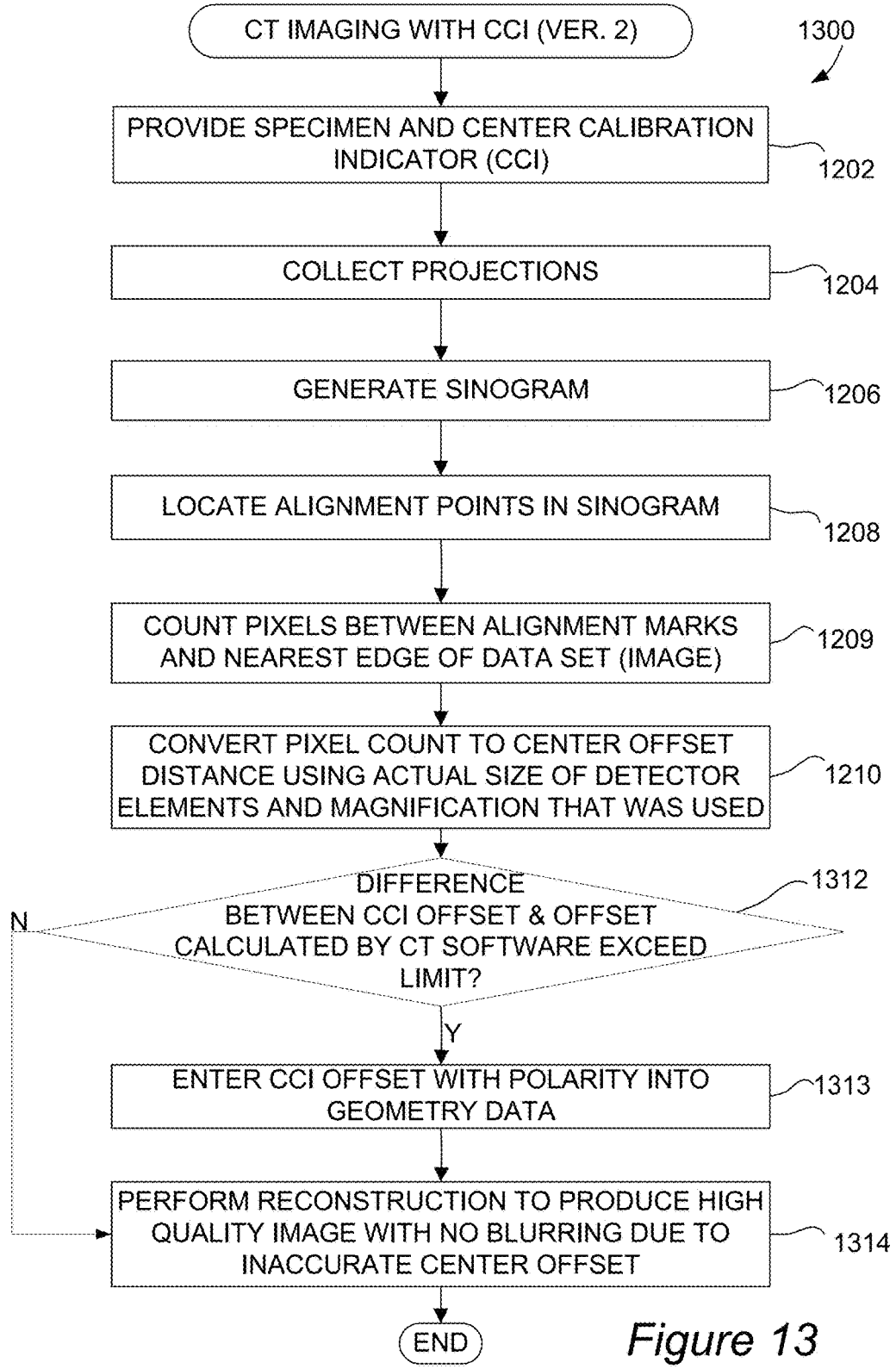
FIG. 13 is a flow chart illustrating an alternative process for performing CT imaging in accordance with another embodiment of the invention.

FIG. 13 is a flow chart illustrating an alternative process for performing CT imaging in accordance with another embodiment of the invention. This process 1300 is similar to the process 1200 of FIG. 12A, e.g., the similarly labelled steps are performed the same. However, after the offset is determined in operation 1210, it may be determined whether the difference between the CCI offset and the offset calculated by the CT software exceeds a predefined limit in operation 1312. For example, the CT may include software for determining center offset via other techniques that do not use the CCI, such as determining the center line of the entire sinogram image by finding a line of balance of the pixel grayscale values.

If the difference between offset does not exceed the limit, the reconstruction may be performed with the calculated CT software's offset in operation 1314. If the limit is exceeded, the CCI offset with the polarity may be entered into the geometry data in operation 1313, and the reconstruction is performed using this new offset in operation 1314. The procedure then ends. However, this process 1300 may be repeated for any number of sub-portions and positions of the specimen.

Reconstruction Techniques

Any suitable technique for forming sinogram images and reconstructing the specimen image may be implemented. In general, a determined center offset error may be used in the reconstruction process to correct the position of the projections relative to each other. The projections may then be used during reconstruction to create the volume data set for the object being scanned.

Figure 14A:
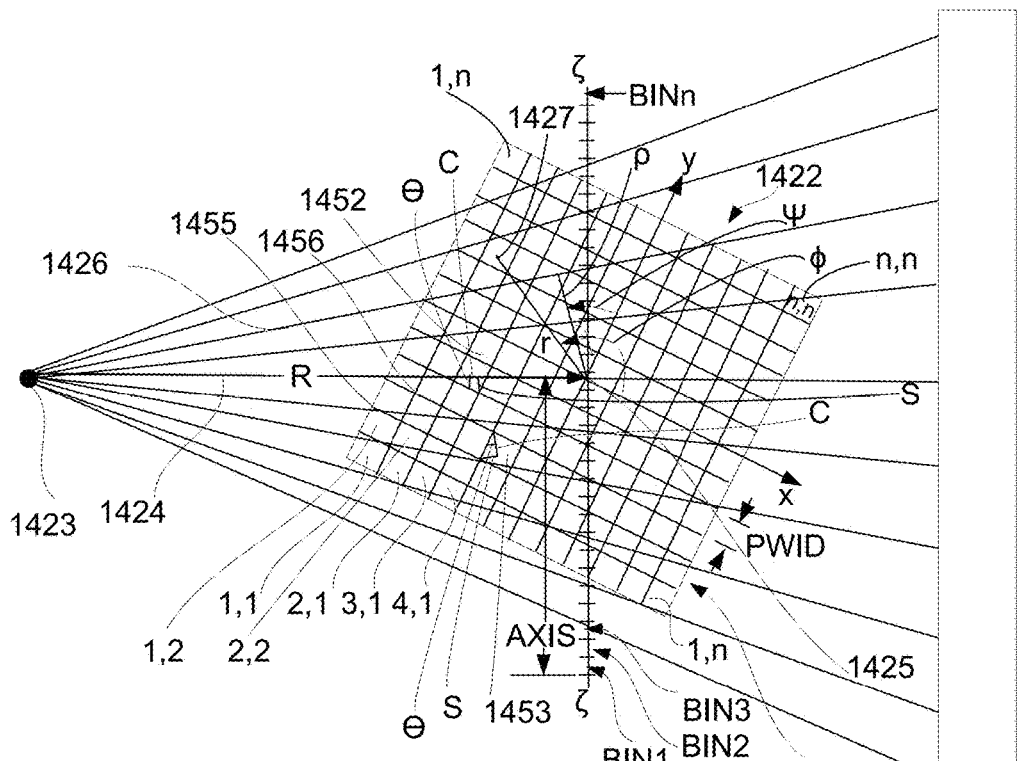
FIG. 14A is a diagrammatic representation of CT system for illustrating image reconstruction.

FIG. 14A is a diagrammatic representation of a CT system for illustrating image reconstruction. While the mechanics for taking the projections in the above-described exemplary equipment can and do vary, the common thread binding all the systems is the creation of a projection space and the taking of a plurality of projections at a plurality of angles around the projection space. Some reconstruction algorithms assume that the projections are all intended to be centered at a center of rotation on the vertical centerline of the detector. In one example, the midline is defined as the projection of the focal point onto the detector (e.g. on a ray through the turn table or specimen support pivot point and normal to the detector). It will be appreciated that in practice, the projection may not have a centerline that aligns with the turntable pivot point and the center of the spot of origin of the radiation rays.

Turning again to FIG. 14A, the detector 1406 may be a gamma camera having a crystal face, which receives a fan of rays directed through the specimen from the focal spot 1423 for each transaxial slice. The apex 1423 of the fan and its swath are indicated in FIG. 14A. The image space is represented by the pixelized area 1422 which can be conceptualized as disposed between the focal spot and the detector arrangement. In the actual scanning apparatus, the image space is occupied by the specimen being scanned from which a set of projections is formed. The geometry of FIG. 14A relates the image space to the projections which are collected by the detectors, and after processing, are mapped into the image space to form the reconstructed image.

With respect to the geometry, it is seen that the image space is based on an xy-coordinate system with the origin located at the center of rotation 1425 of the system, a fixed distance R from the focal point. FIG. 14A illustrates a square pixel array with each pixel of width PWID (measured in units of projection bin width implying that the architecture has been scaled so that distance between adjacent detector bins is unity), having an $(x_i, y_j)$ coordinate with i and j ranging from 1 through n, where n is the index of the last element of a row or column of the display as indicated in FIG. 14A. The single projection illustrated in FIG. 14A is taken at an angle $\Theta$ with respect to the xy coordinate system.

In a system involving parallel beam geometry, all rays in the projection would be parallel to the center ray 1424, simplifying the reconstruction process. However, in the fan beam case illustrated in FIG. 14A, the rays diverge from the focal point 1423 in a fan shaped swath toward the detector. Taking ray 1426 as exemplary, it can be identified in coordinates for parallel beam geometry by the normal $\rho$ drawn from the origin to the ray and the angle $\psi$ formed between the coordinate system and $\rho$. Similarly, any arbitrary point in the reconstruction space, such as point 1427, can be identified by its polar coordinates $(r, \phi)$.

In order to simplify the reconstruction process in a true fan beam system, another coordinate system based on the $\zeta$ axis which, as shown in FIG. 14A, is normal to central ray 1424 and intersects the center of rotation. The $\zeta$ axis defines a set of projection bins 1 through n, where bin n is the last bin, of unit width whose projection information is derived from the detector cells in accordance with the diverging geometry of the fan. Any ray in the fan can be identified by the coordinates $(\zeta, \Theta)$. Thus, a fan beam projection can be identified by $\rho(\zeta, \Theta)$.

When the coordinates of the projections are remapped from parallel beam to account for the diverging nature of the fan beam, the projection bins must be scaled with a geometric factor. More particularly, examining the geometry shown in FIG. 14A, it can be shown that:

$$\frac{\rho}{R} = \frac{\zeta}{\sqrt{(R^2 + \zeta^2)}} \qquad \text{Equation 1}$$

Rearranging, and relating the differential $d\rho$ to the differential $d\zeta$ yields:

$$d\rho = \frac{R^3}{(R^2 + \zeta^2)^{3/2}} d\zeta \qquad \text{Equation 2}$$

Thus, a unit change of $\rho$ does not yield a unit change of $\zeta$, but a change weighted by the factor indicated in Equation 2. In fan beam reconstruction algorithms, the projections are appropriately weighted to take account of this geometric factor. However, when the center of rotation of the system is shifted the weighting factors are no longer valid and use of reconstruction procedures may generate artifacts.

Figure 14B:
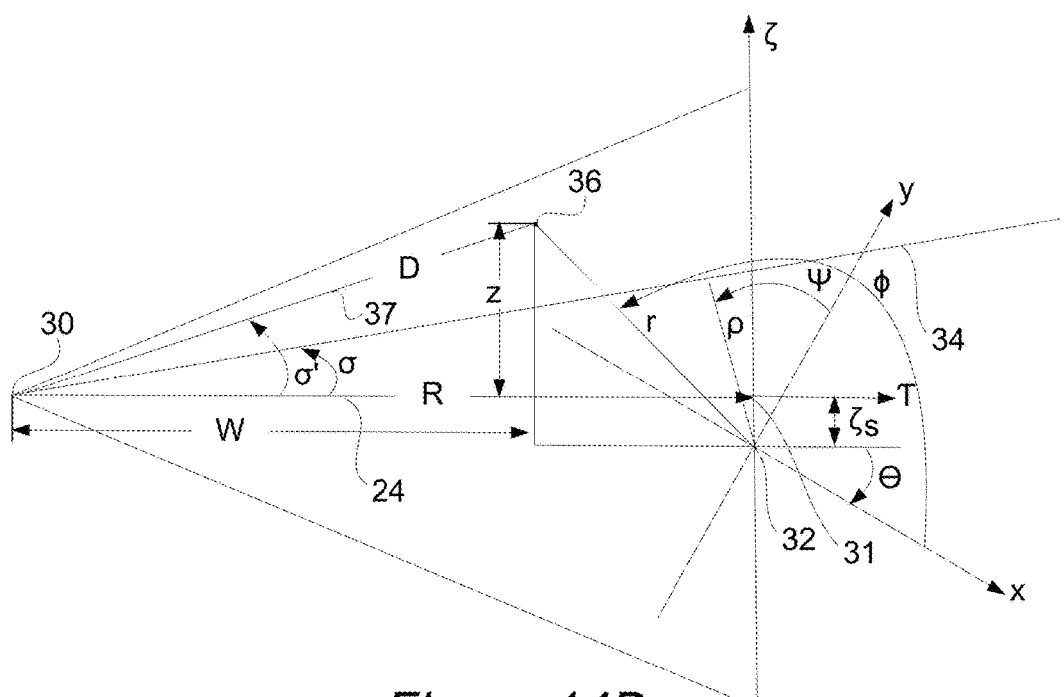
FIG. 14B illustrates the geometry for a fan beam CT system in which the center of rotation is shifted.

Turning now to FIG. 14B, there is shown the geometry for a fan beam CT system in which the center of rotation is shifted. Central ray 24 emanates from the focal point 30 and normal to the detector (not shown), intersecting the $\zeta$ axis at a point 31 assumed by conventional fan beam algorithms to be the center of the coordinate system $(r, \xi)$. The distance R is that measured between the focal spot 30 and the point 31. The actual center of rotation may be off-center, shown as point 32 which would then be the actual origin of the rotating xy coordinate system, and is displaced along the $\zeta$ axis by a fixed amount $\zeta_s$ representing the shift. A typical ray 34 within the fan is shown as having parallel beam projection coordinates (ρ, ψp). Similarly, any arbitrary point within the reconstructed image can be denoted by its polar coordinates (r, φ).

A term ζ' may be defined as R tan, which is the intersection of the ray 37 with the axis ζ as shown in FIG. 14B. It is also possible considering the trigonometric relationship of the triangles sharing the common angle σ' to define ζ' as follows:

$$\zeta' = \frac{R(r\sin(\phi - \theta) + \zeta)}{R + r\cos(\phi + \theta)} \quad \text{Equation 3}$$

This expresses in terms of the coordinates (r, φ) and variable Θ. Radon's inversion formula which integrates over the fan beam projection coordinates (ζ,Θ) can be expressed as follows:

$$f(r, \phi) = \frac{1}{4\pi^2} \int_0^{2\pi} g'(\zeta', \theta) \frac{R^2}{(R + r\cos(\phi - \theta))^2} d\theta \quad \text{Equation 4}$$

$$g'(\zeta', \theta) = \lim_{\varepsilon \to 0} \int F_\varepsilon(\zeta - \zeta') p(\zeta, \theta) \left[ \frac{(1 + \zeta\zeta_s/R^2)}{(1 + \zeta^2/R^2)^{1/2}} \right] d\zeta \quad \text{Equation 5}$$

It will now be appreciated that the foregoing expressions 3, 4 and 5 provide the basis for a procedure whereby projections taken with a shift in the center of rotation are weighted by a factor which takes into account the shift, the weighting factor being:

$$\frac{(1 + \zeta\zeta_s/R^2)}{(1 + \zeta^2/R^2)^{1/2}} \quad \text{Equation 6}$$

The so weighted projections are convolved according to the integral of expression 5, and the modified projections g'(ζ',Θ) back projected according to expression 4 to produce the reconstructed image derived from Radon's inversion formula.

In practice, the continuous analytic reconstruction solution set forth in expressions 4 and 5 can be implemented in discrete digital sampled data format in high speed digital computers. Such adaptation of the analytic reconstruction uses the introduction of approximations dealing, for example, with sampling considerations with regard to the kernel used to filter the weighted projection data, and the conversion of the sampled filtered projections to continuously sampled filtered projections.

In general, the relationships developed above may be applied in a digital sampled data system for processing of projections taken in a rotating fan beam system in which the center of rotation is shifted from not adversely affect the quality of images obtained with the midline of the fan beam. A weighting function is developed from expression 6 which is a function of system geometry and the magnitude of the shift. Transforming expression 6 to the digitally implemented case in which the projection p(k,Θ$_m$) is a function of the projection bin k and the view angle Θ$_m$, the weighting function for all views as a function of k is defined as:

$$d(k) = \frac{1 + l\zeta_s/R^2}{(1 + l^2/R^2)^{1/2}} \quad \text{Equation 7}$$

where I=FIX(k-AXIS). The offset AXIS shown in FIG. 14A allows the definition of projection bins beginning at 1 for the first bin. FIX simply indicates that the value in parenthesis is integerized. The projection data p (k,Θ$_m$) for each view is modified by the weighting function d(k) to provide a weighted projection g(k,Θ$_m$) as follows:

$$g(k,\Theta_m) = d(k)p(k,\Theta_m)$$

The discrete values of F(k) are given, within a scale factor used to normalize the final reconstruction, by:

$$F(k) = \begin{cases} \dfrac{\pi}{2} & \text{if } k = 0 \\ -\dfrac{1}{\pi k^2} & \text{if } k \text{ odd} \\ 0 & \text{if } k \text{ even} \end{cases} \quad \text{Equation 8}$$

Thus, the convolution of the modified projection set using the desired filter can be expressed as follows:

$$g'(k, \theta_m) = \sum_{k'} F(k - k') g(k', \theta_m) \quad \text{Equation 9}$$

In practice, the convolution may be performed using Fast Fourier Transform (FFT) operations incorporating the FFT of the kernel and the FFT of the sampled projection. Because of noise and aliasing the kernel may be rolled off using a suitable window.

Each projection set is convolved independently and stored until the modified convolved projection sets are mapped into pixelated space in accordance with the back projection operation. The actual back projection operation uses all values of the filtered projections over a specified range, in contrast to the discrete samples provided by the filtration operation. Typically, the sampled filtered projections are effectively converted to continuously sampled projections using linear interpolation. In the following digital implementation, linear interpolation will be used, appreciating that it is only an approximation to the exact "sine" interpolation that may be used to restore a band-limited sampled signal. In some applications, higher ordered interpolation schemes might be used.

The back projection of the modified convolved projections into pixelated space (x$_i$, y$_j$) can be expressed as Equation 10:

$$f(x_i, y_j) = \frac{1}{NANG} \sum_{m=1}^{NANG} [f_k g'(k, \theta_m) + (1 - f_k) g'(k+1, \theta_m)]$$

$$x \left[ \frac{R^2}{(R + x_i \cos\theta_m + y_i \sin\theta_m)} \right]$$

where k=FIX(ζ'+AXIS), (1−f$_k$)+ζ'+AXIS−k and ζ' axis is given by equation 3. The contribution from the discrete modified projections g'(k, Θ$_m$) may be determined by interpolating between adjacent projection bins, in the present example using linear interpolation. The shift parameter may be accounted for in the back projection by appropriately defining the projection bin k as well as the interpolation factor f$_k$ to account for the shift.

In equation 10, the summation signifies a summation of views for all angles from 1 through NANG. Using linear interpolation, a partial contribution $f_k$ g'(k, $\Theta_m$) may be determined from the $k^{th}$ modified projection bin for the particular projection $\Theta_m$ and the remaining contribution $(1-f_k)$ g'(k+I,$\Theta_m$) from the $(k+1)^{th}$ modified projection bin. The factor in the continuous analytic solution (equation 4 transformed into pixelated coordinates is defined here as 1/U2:

$$\frac{1}{U2} = \frac{R^2}{(R + x_i \cos\theta_m + y_i \sin\theta_m)} \qquad \text{Equation 11}$$

The illustrated back projection can be performed using a special purpose hardware processor, as well as in a general purpose computer. In general, the process may operate on each projection set in turn (each $\Theta$), and for each projection set determine the contribution to each pixel B(I,J) based on linear interpolation between adjacent projection bins as determined by the process. In implementing expression 10, the reconstruction $f(x_i, y_j)$ will be stored in the array B(I,J).

The process may first select a first projection set and zero the array B(I,J). Various factors are evaluated which allow the Z (vertical) and W (horizontal) coordinates to be incremented by simple sums and differences. The S and C parameters which are evaluated can be better appreciated with reference to FIG. 14A. It will be recalled that the pixelized space in FIG. 14A is illustrated at an angle $\Theta$ with respect to the $\zeta$ axis. Thus, any line drawn through a pixel which is either parallel to the $\zeta$ axis or parallel to ray R (which in turn is perpendicular to the $\zeta$ axis) and intersects the corner of a pixel will form an angle $\Theta$ with the pixel edge. A right triangle can be formed with the pixel edge (whose dimension is PWID) and the S parameter will be the length of the side opposite the angle $\Theta$. Similarly, the C parameter will be the length of the side adjacent the angle $\Theta$. In FIG. 14A, the pixel 1452 shows a triangle having its C side parallel to R, and the pixel 1453 illustrates a similar triangle having its C side parallel to the $\zeta$ axis.

S+C represents the length between the projection of two corners of a pixel (such as corners 1455, 1456) onto the ray R, while S–C represents the length between the projection of the same two corners onto the $\zeta$ axis. Multiplying those projections by n/2 creates projections onto the ray R and $\zeta$ axis equal to the distance from the lower left corner of the pixel (1,1) to the origin. The ZZ and WW values are the initial values for Z and W parameters shown in FIG. 14B. As will become apparent, those values are updated for each pixel to give correct Z and W values for each pixel.

The projection onto the $\zeta$ axis, identified as ZZ, is altered by the value of the shift, by adding the shift $\zeta_s$ that has been incremented. By modifying the back projection geometry with the shift, the previously modified weighted convolved projection sets can be back projected to produce a result wherein both the convolution and back projection are compensated for the shift to produce accurate reconstructions in spite of the shift.

Having now established the initial parameters for the view angle $\Theta$, the pixel row index J is initialized. ZZ and WW coordinates identifying the particular row of pixels being back projected at that point in the process are provided. As will become apparent, those coordinates may be altered only when the back projection switches from one row to another in the pixelized space.

The pixel column index I is set, and temporary parameters Z and W may be defined to be incremented as the back projection proceeds along a row of pixels. The Z and W parameters are incremented in dependence on the S and C values for the $\Theta$ in question. Thus, the result is to identify parameters related to Z and W for a particular pixel, in the present instance the first pixel in the back projection array B(I,1). The projection bins which contribute to the pixel in question are identified, and the factor U2 is evaluated. More particularly, in evaluating ZF it is seen that the ratio of Z to W is taken then multiplied by R to define the projection of the point in question on the $\zeta$ axis. That point is offset by AXIS which as shown in FIG. 14A is simply an offset which allows the definition of projection bins beginning at 1 for the first bin. The step then defines the projection bins which contribute to the pixel by setting bin index K=FIX(ZF).

The inverse of the factor U2 is evaluated by simply squaring the ratio of W over R. On reference to FIG. 14B, that operation yields the inverse of the factor specified in equation 11. In addition, the factor is divided by PWID. Processing to this point had been accomplished in units of projection bins. In building up image for display, a conversion to units of pixel width may be performed. In emission computed tomography, the units may be defined in terms of counts per unit area; as such, when the back projector is used for emission computed tomography, a division factor of PWID$^2$ may be used.

Having identified the projection bin and the U2 factor, the process proceeds to define a center ray 24 for the midline of the actual back projection. The information previously resident in the memory location for the pixel (I,J), that is B(I,J) is updated by adding an amount linearly interpolated from the K and K+1 projection bins. A proportion of the information in projection bin K, P(K), determined by the difference between the floating point coordinate of projection bin K+1 and ZF, is added to a proportion of the information within projection bin K+1, P(K+1), determined by the difference ZF and the floating point coordinate of projection bin K. That sum is divided by U2, and the result added to B(I,J) to update the information for the information for the pixel in question.

Following the back projection evaluation for the first pixel, the column index I is incremented, the Z and W coordinates are then determined for the next pixel in the row. The evaluation step is again performed, and the back projection operation is then accomplished for that pixel. That loop continues to cycle until it is determined that all columns within the first row have been updated, whereupon the row index J is incremented. The temporary ZZ and WW coordinates are updated before processing the second row. The column index I is again set to 1 and Z and W are redefined in accordance with the coordinates of the first pixel in the second row. The back projection operation may then be performed for all pixels in the second row. The row index J is incremented, and all pixels in that row are back projected until all pixels in the array have been processed. At that point, $\Theta$ is incremented to select the next view for processing. In effect, the xy-coordinate system is rotated to the new view angle $\Theta$, and the process is repeated for the new view. The process proceeds as described above until contributions are made to all pixels for each view and all views have been processed, whereupon the back projection operation is terminated. The pixelized space at that point contains information back projected from all views such that a display of the information in the pixelized memory produces an image of the cross-section which created the original projections.

Examples of Aircraft and Methods of Fabricating and Operating Aircraft

Figure 15A:
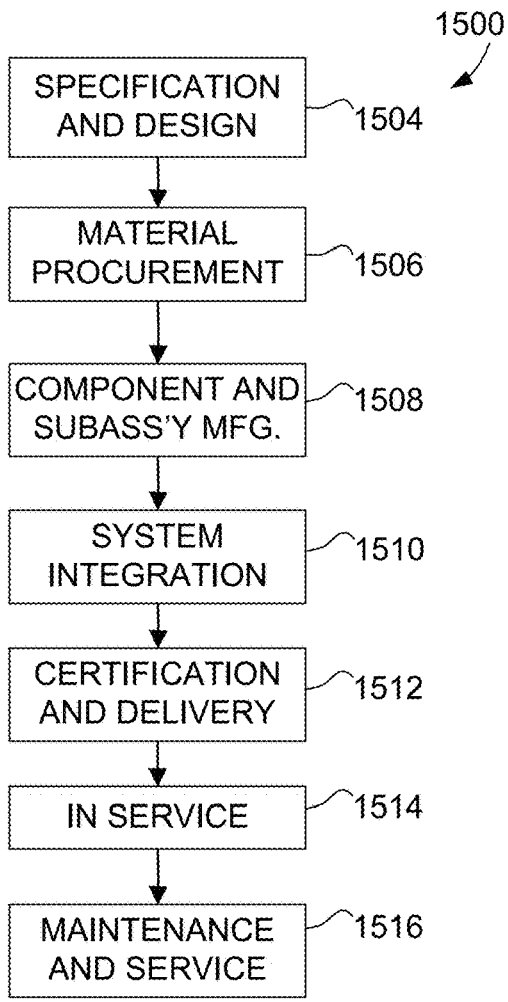
FIG. 15A is a flowchart of aircraft manufacturing and use, in accordance with some embodiments.
Figure 15B:
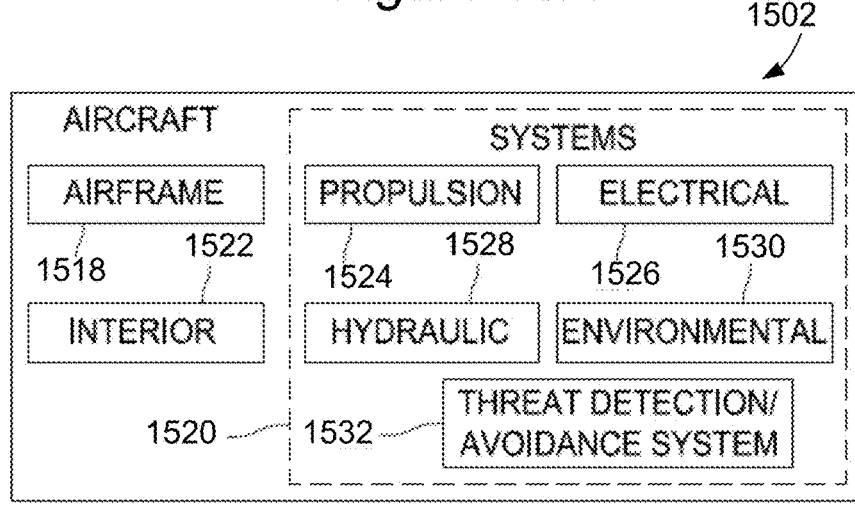
FIG. 15B is a block diagram of aircraft systems, in accordance with some embodiments.

Examples of the present disclosure may be described in the context of aircraft manufacturing and service method 1500 as shown in FIG. 15A and aircraft 1502 as shown in FIG. 15B.

FIG. 15A is a flowchart of aircraft manufacturing and use, in accordance with some embodiments. During pre-production, illustrative method 1500 may include block 1504, specification and design of aircraft 1502 and block 1506, material procurement. During production, block 1508 of component and subassembly manufacturing and block 1510 of inspection system integration of aircraft 1502 may take place. Thereafter, aircraft 1502 may go through block 1512 of certification and delivery to be placed in service at block 1514. While in service, aircraft 1502 may be scheduled for block 1516, routine maintenance and service. Routine maintenance and service may include modification, reconfiguration, refurbishment, etc. of aircraft 1502.

Each of the processes of illustrative method 1500 may be performed or carried out by an inspection system integrator, a third party, and/or an operator (e.g., a customer). For the purposes of this description, an inspection system integrator may include, without limitation, any number of aircraft manufacturers and major-inspection system subcontractors; a third party may include, without limitation, any number of vendors, subcontractors, and suppliers; and an operator may be an airline, leasing company, military entity, service organization, and so on.

FIG. 15B is a block diagram of aircraft systems, in accordance with some embodiments. Aircraft 1502 produced by illustrative method 1500 may include airframe 1518 with a plurality of high-level inspection systems 1520 and interior 1522. Examples of high-level inspection systems 1520 include one or more of propulsion inspection system 1524, electrical inspection system 1526, hydraulic inspection system 1528, and environmental inspection system 1530. Any number of other inspection systems may be included. Although an aerospace example is shown, the principles disclosed herein may be applied to other industries, such as the automotive industry. Accordingly, in addition to aircraft 1502, the principles disclosed herein may apply to other vehicles, e.g., land vehicles, marine vehicles, space vehicles, etc.

Apparatus and methodology shown or described herein may be employed during any one or more of the stages of manufacturing and service method 1500. For example, components or subassemblies corresponding to block 1508, component and subassembly manufacturing, may be fabricated or manufactured in a manner similar to components or subassemblies produced while aircraft 1502 is in service as in block 1514. Also, one or more examples of the apparatus, methodology, or combination thereof may be utilized during production stages illustrated by block 1508 and block 1510, for example, by substantially expediting assembly of or reducing the cost of aircraft 1502. Similarly, one or more examples of the apparatus or method realizations, or a combination thereof, may be utilized, for example and without limitation, while aircraft 1502 is in service as in block 1514 and/or during maintenance and service as in block 1516.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method (1200, 1300) of determining a center offset distance for computed tomography "CT" imaging, the method comprising:
   providing (1202) a specimen (108) on a support (104) that is positioned between an emission source (102) for outputting radiation towards the specimen while the specimen rotates with respect to a detector (112, 1272) for receiving radiation that has passed through the specimen;
   providing (1202) a center calibration indicator "CCI" (907, 1260) positioned near the specimen so that at least a portion of the radiation passes through the CCI and impinges on the detector;
   collecting (1204) projection data (1406) from emissions received at the detector for a plurality of rotational positions of the specimen relative to the detector;
   generating (1206) a sinogram image (1100) based on the projection data;
   locating (1208) two alignment points (1102*a*, 1102*b*) corresponding to the CCI in the sinogram image;
   determining (1210) the center offset distance for the sinogram image based on the two alignment points; and
   reconstructing (1212, 1314) an image (110) of the specimen from the sinogram image using the determined center offset distance.

2. The method of claim 1, wherein the center offset distance is determined by comparing a center (304, 112*a*, 31) of the sinogram image to a midway position (32) between the two located alignment points.

3. The method of claim 1, wherein the CCI is sized and shaped to result in two opposing points of contrast in the sinogram image that together accurately depict the center offset distance.

4. The method of claim 1, wherein the CCI has a different density than the specimen.

5. The method of claim 1, wherein the CCI is a thin rectangular object having a significantly longer length than thickness.

6. The method of claim 1, wherein the center offset distance is determined by:
   counting (1209) a first number of pixels from a first one of the two located alignment points to a closest edge of the sinogram image;
   converting (1210) the first pixel number into a first distance based on a size of the detector and a magnification of the projection data;
   counting (1209) a second number of pixels from a second one of the two located alignment points to a closest edge of the sinogram image;
   converting (1210) the second pixel number into a second distance based on a size of the detector and a magnification of the projection data; and
   comparing (1210) the first distance to the second distance to obtain the center offset distance, including polarity.

7. The method of claim 1, wherein the center offset distance is determined to correspond to a fraction of a detector element of the detector.

8. The method of claim 1, wherein reconstructing the image of the specimen includes entering the offset distance, including its polarity, into geometry data for the sinogram image.

9. The method of claim 1, wherein reconstructing the image of the specimen includes:

determining (1312) whether the determined offset distance differs by a predefined limit from an offset calculated by a CT technique that is not based on the CCI;

reconstructing (1314) the image using the CT technique's calculated offset if the predefined limit is not exceeded; and reconstructing (1313, 1314) the image using the determined center offset distance if the predefined limit is exceeded.

10. The method of claim 1, wherein the CCI is attached to the specimen, and the CCI is sized so that radiation passes through an entire length of the CCI at two rotational positions corresponding to the two alignment points being attenuated more than other points in the sinogram image.

11. A computed tomography (CT) system, comprising:
an emission source (102) for outputting radiation towards a specimen (108);
a support (104) for placement of the specimen (108) and that is rotatable, wherein a center calibration indicator (CCI) (907, 1260) positioned near the specimen so that at least a portion of the radiation passes through the CCI and impinges on a detector (112, 1272);
the detector for receiving radiation that has passed through the specimen and CCI; and
a processor (1050b) and memory (1050a) configured for performing the following operations:
collecting (1204) projection data (1406) from emissions received at the detector for a plurality of rotational positions of the specimen relative to the detector;
generating (1206) a sinogram image (1100) based on the projection data;
locating (1208) two alignment points (1102a, 1102b) corresponding to the CCI in the sinogram image;
determining (1210) a center offset distance for the sinogram image based on the two alignment points; and
reconstructing (1212, 1314) an image of the specimen from the sinogram image using the determined center offset distance.

12. The system of claim 11, wherein the CCI is positioned and sized so as to facilitate accurate determination of the center offset distance.

13. The system of claim 11, wherein the CCI is sized and shaped to result in two opposing points of contrast in the sinogram image that together accurately depict the center offset distance.

14. The system of claim 11, wherein the CCI has a different density than the specimen.

15. The system of claim 11, wherein the CCI is a thin rectangular object having a significantly longer length than thickness.

16. The system of claim 11, wherein the center offset distance is determined by:
counting a first number of pixels from a first one of the two located alignment points to a closest edge of the sinogram image;
converting the first pixel number into a first distance based on a size of the detector and a magnification of the projection data;
counting a second number of pixels from a second one of the two located alignment points to a closest edge of the sinogram image;
converting the second pixel number into a second distance based on a size of the detector and a magnification of the projection data; and
comparing the first distance to the second distance to obtain the center offset distance, including polarity.

17. The system of claim 11, wherein the center offset distance is determined to correspond to a fraction of a detector element of the detector.

18. The system of claim 11, wherein reconstructing the image of the specimen includes entering the center offset distance, including its polarity, into geometry data for the sinogram image.

19. The system of claim 11, wherein reconstructing the image of the specimen includes:
determining whether the determined offset distance differs by a predefined limit from an offset calculated by a CT technique that is not based on the CCI;
reconstructing the image using the CT technique's calculated offset if the predefined limit is not exceeded; and
reconstructing the image using the determined center offset distance if the predefined limit is exceeded.

20. The system of claim 11, wherein the CCI is attached to the specimen, and the CCI is sized so that radiation passes through an entire length of the CCI at two rotational positions corresponding to the two alignment points being attenuated more than other points in the sinogram image.

* * * * *